US008361722B2

(12) United States Patent
Croce

(10) Patent No.: US 8,361,722 B2
(45) Date of Patent: Jan. 29, 2013

(54) METHOD FOR DIAGNOSING ACUTE LYMPHOMIC LEUKEMIA (ALL) USING MIR-221

(75) Inventor: Carlo M. Croce, Columbus, OH (US)

(73) Assignee: The Ohio State University Research Foundation, Columbus, OH (US)

(*) Notice: Subject to any disclaimer, the term of this patent is extended or adjusted under 35 U.S.C. 154(b) by 0 days.

(21) Appl. No.: 13/274,719

(22) Filed: Oct. 17, 2011

(65) Prior Publication Data
US 2012/0046192 A1 Feb. 23, 2012

Related U.S. Application Data

(62) Division of application No. 12/664,531, filed as application No. PCT/US2008/066870 on Jun. 13, 2008, now Pat. No. 8,053,186.

(60) Provisional application No. 60/934,707, filed on Jun. 15, 2007.

(51) Int. Cl.
C12Q 1/68 (2006.01)
(52) U.S. Cl. ........................................................ 435/6.1
(58) Field of Classification Search .................... 435/6.1
See application file for complete search history.

(56) References Cited

U.S. PATENT DOCUMENTS

| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 7,888,010 B2 | 2/2011 | Brown et al. |
| 7,919,245 B2 | 4/2011 | Brown et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |

(Continued)

FOREIGN PATENT DOCUMENTS

| CA | 2533701 A1 | 2/2005 |
| CA | 2587189 | 12/2006 |

(Continued)

OTHER PUBLICATIONS

Kotani et al. The American Society of Hematology 2009, vol. 114, pp. 4169-4178.*
Australian Office Action, Application No. 2006291165 dated Feb. 13, 2012.
Australian Office Action, Application No. 2007205257 dated Dec. 22, 2011.
Australian Office Action, Application No. 2007205234 dated Sep. 20, 2011.
Canadian Office Action, Application No. 2,635,616, dated Feb. 27, 2012.
Canadian Office Action, Application No. 2,617,581, dated Apr. 2, 2012.
Chinese Office Action, Application No. 20088011920639 dated May 3, 2012.

(Continued)

Primary Examiner — Brian Whiteman
(74) Attorney, Agent, or Firm — MacMillan, Sobanski & Todd, LLC

(57) ABSTRACT

Disclosed are compositions and methods for reducing the proliferation of ALL cancer cells through targeted interactions with ALL1 fusion proteins.

6 Claims, 13 Drawing Sheets

U.S. PATENT DOCUMENTS

| | | |
|---|---|---|
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0127895 A1 | 6/2006 | Sabapathy |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306016 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004322 A1 | 1/2010 | Croce |
| 2010/0048681 A1 | 2/2010 | Croce |
| 2010/0099200 A1 | 4/2010 | Nazabal et al. |
| 2010/0104662 A1 | 4/2010 | Oren et al. |
| 2010/0120898 A1 | 5/2010 | Croce et al. |
| 2010/0137410 A1 | 6/2010 | Croce |
| 2010/0144850 A1 | 6/2010 | Croce |
| 2010/0173319 A1 | 7/2010 | Croce et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0196426 A1 | 8/2010 | Skog et al. |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0317610 A1 | 12/2010 | Croce |
| 2011/0015080 A1* | 1/2011 | Golub et al. .................. 506/2 |

FOREIGN PATENT DOCUMENTS

| | | |
|---|---|---|
| FR | 2877350 | 5/2006 |
| WO | 9015156 | 12/1990 |
| WO | 9100364 | 1/1991 |
| WO | 9107424 | 5/1991 |
| WO | 9312136 | 6/1993 |
| WO | 9410343 | 5/1994 |
| WO | 9424308 | 10/1994 |
| WO | 9426930 | 11/1994 |
| WO | 9613514 | 5/1996 |
| WO | 9635124 | 11/1996 |
| WO | 9729119 | 8/1997 |
| WO | 9809510 | 3/1998 |
| WO | 0003685 | 1/2000 |
| WO | 0050565 | 8/2000 |
| WO | 0055169 | 9/2000 |
| WO | 0076524 | 12/2000 |
| WO | 0144466 | 6/2001 |
| WO | 0168666 | 9/2001 |
| WO | 0177343 | 10/2001 |
| WO | 0187958 | 11/2001 |
| WO | 02064171 | 8/2002 |
| WO | 02064172 | 8/2002 |
| WO | 03029459 | 4/2003 |
| WO | 03078662 | 9/2003 |
| WO | 03092370 | 11/2003 |
| WO | 2004033659 | 4/2004 |
| WO | 2004043387 | 5/2004 |
| WO | 2004079013 | 9/2004 |
| WO | 2004079377 | 11/2004 |
| WO | 2005013901 A3 | 2/2005 |
| WO | 2005017711 | 2/2005 |
| WO | 2005020795 | 3/2005 |
| WO | 2005060661 | 7/2005 |
| WO | 2005078139 | 8/2005 |
| WO | 2005079397 A2 | 9/2005 |
| WO | 2005080601 | 9/2005 |
| WO | 2005103298 A2 | 11/2005 |
| WO | 2005118806 | 12/2005 |
| WO | 2006105486 | 10/2006 |
| WO | 2006108718 | 10/2006 |
| WO | 2006119266 | 11/2006 |
| WO | 2006133022 | 12/2006 |
| WO | 2006137941 | 12/2006 |
| WO | 2007016548 | 2/2007 |
| WO | 2007016548 A2 | 2/2007 |
| WO | 2007033023 | 3/2007 |
| WO | 2007044413 | 4/2007 |
| WO | 2007081680 | 7/2007 |
| WO | 2007081720 | 7/2007 |
| WO | 2007081740 | 7/2007 |
| WO | 2007084486 | 7/2007 |
| WO | 2007109236 | 9/2007 |
| WO | 2007112097 | 10/2007 |

| | | |
|---|---|---|
| WO | 2007112754 A2 | 10/2007 |
| WO | 2007/127190 | 11/2007 |
| WO | 2008008430 | 1/2008 |
| WO | 2008/036168 A2 | 3/2008 |
| WO | 2008036776 | 3/2008 |
| WO | 2008054828 | 5/2008 |
| WO | 2008070082 | 6/2008 |
| WO | 2008073915 | 6/2008 |
| WO | 2008073920 | 6/2008 |
| WO | 2008094545 | 8/2008 |
| WO | 2008097277 | 8/2008 |
| WO | 2008136971 | 11/2008 |
| WO | 2008153987 | 12/2008 |
| WO | 2008157319 | 12/2008 |
| WO | 2009018303 | 2/2009 |
| WO | 2009020905 | 2/2009 |
| WO | 2009026487 | 2/2009 |
| WO | 2009033140 | 3/2009 |
| WO | 2009049129 | 4/2009 |
| WO | 2009055773 | 4/2009 |
| WO | 2009064590 | 5/2009 |
| WO | 2009070653 | 6/2009 |
| WO | 2009100029 | 8/2009 |
| WO | 2009108853 | 9/2009 |
| WO | 2009108856 | 9/2009 |
| WO | 2009108860 | 9/2009 |
| WO | 2009108866 | 9/2009 |
| WO | 2009152300 | 12/2009 |
| WO | 2010019694 | 2/2010 |
| WO | 2010059779 | 5/2010 |
| WO | 2010065156 | 6/2010 |
| WO | 2010099161 | 9/2010 |

OTHER PUBLICATIONS

Communication Concerning Office Action Received from Japanese Patent Office dated Jan. 30, 2012, Japanese Patent Application No. 2008-531200.
EP Search Report, Application No. 11196256.9 dated Feb. 28, 2012.
EP Search Report, Application No. 11196262.7 dated Feb. 28, 2012.
EP Search Report, Application No. 11196254.4 dated Feb. 28, 2012.
EP Search Report, Application No. 11196265.0 dated Mar. 5, 2012.
EP Search Report, Application No. 11196261.9 dated Feb. 28, 2012.
EP Search Report, Application No. 11196190.0 dated Apr. 24, 2012.
EP Search Report, Application No. 11196250.2 dated Apr. 24, 2012.
EP Search Report, Application No. 11196253.6 dated Apr. 24, 2012.
EP Search Report, Application No. 11196264-3 dated Feb. 28, 2012.
European Communication Pursuant to Article 94(3) EPC, Application No. 08799295.4, dated Nov. 18, 2011.
European Communication Pursuant to Article 94(3) EPC, Application No. 08767439.6, dated Feb. 12, 2011.
European Communication Pursuant to Article 94(3) EPC, Application No. 07867402.5, dated Apr. 10, 2012.
European Communication Pursuant to Article 94(3) EPC, Application No. 07717903.4, dated Apr. 25, 2012.
European Communication Pursuant to Article 94(3)EPC, Application No. 06814375.9 dated Oct. 14, 2011.
European Communication Pursuant to Article 94(3) EPC, Application No. 06800599.0 dated Nov. 25, 2011.
European Search Report, Application No. 08770974.4, dated Oct. 21, 2011.
Japanese Office Action dated Feb. 24, 2012, Japanese Patent Application No. 2008-549555.
Japanese Office Action dated Feb. 24, 2012, Japanese Patent Application No. 2008-549532.
Japanese Office Action dated Jan. 4, 2012, Japanese Patent Application No. 2008-5251070.
Japanese Office Action dated Feb. 22, 2012, Japanese Patent Application No. 2008-549549.
PCT international Search Report and the Written Opinion, PCT/US2012/020911 filed Jan. 11, 2012, dated Apr. 25, 2012.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Braun et al., "p53-Responsive MicroRNAs 192 and 215 are Capable of Inducing Cell Cycle Arrest," Cancer Research, 2008, pp. 10094-10104, vol. 68.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Gang, M. et al., "Expression of Programmed Cell Death 4 and Its Clinicopathological Significance in Human Pancreatic Cancer," Abstract, 2005, pp. 597-600, vol. 27.
Jazbutyte, V. et al., "MicroNRA-21: From Cancer to Cardiovascular Disease," Current Drug Targets, Abstract, 2010, pp. 926-935, vol. 11.
Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.
Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.
Ribas, J. et al., "The Transcriptional Regulation of miR-21, Its Multiple Transcripts, and Their Implication in Prostate Cancer," Cell Cycle, 2010, pp. 923-929, vol. 9.
Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.
Ryu, J.K. et al., "Aberrant MicroRNA-155 Expression is an Early Event in the Multistep Progression of Pancreatic Adenocarcinoma," Pancreatology, 2010, pp. 66-73, vol. 10.
Stamatopoulos, B. et al., "MicroRNA-29c and MicroRNA-233 Down-Regulation has in Vivo Significance in Chronic Lymphocytic Leukemia and Improves Disease Risk Stratification," Blood, May 2009, pp. 5237-5245, vol. 113, No. 21.
Vassilev et al., "In Vivo Activation of the p53 Pathway by Small-Molecule Antagonists of MDM2," Science, 2004, pp. 844-848, vol. 303.
Watson, D.I. et al., "MicroRNA Expression Profiles in Barrett's Oesophagus," RACS Annual Scientific Congress, 2007, pp. A45, vol. 77.
Wiemer et al., "The Role of MicroRNAs in Cancer: No Small Matter," European Journal of Cancer, Jun. 12, 2007, vol. 43, No. 10, pp. 1529-1544.
Xi, Y. et al., "Prognostic Values of MicroRNAs in Colorectal Cancer," Biomarker Insights, Jan. 2006, pp. 113-121, vol. 1.
Zhao et al., "p53 Mediates the Negative Regulation of MDM2 by Orphan Receptor TR3," The EMBO Journal, 2006, pp. 5703-5715, vol. 25.
PCT International Preliminary Report on Patentability, PCT/US2008/071532 filed Jul. 30, 2008, dated Feb. 2, 2010.
Canadian Office Action, Application No. 2,621,441, dated Feb. 1, 2011.
European Seach Report, Application No. 11151749.6, dated Feb. 8, 2011.
PCT International Preliminary Report on Patentability, PCT/US2009/038214 filed Mar. 25, 2009, dated Jun. 16, 2011.
European Search Report, Application No. 09713926.5 dated Jul. 21, 2011.
European Search Report, Application No. 11151769-4, dated Feb. 8, 2011.
European Search Report, Application No. 11151771-0, dated Feb. 8, 2011.
European Search Report, Application No. 11151772-8, dated Feb. 8, 2011.
European Search Report, Application No. 08713330.2, dated Jul. 22, 2011.
European Search Report, Application No. 08799295.4-2402, PCT/US2008/075565, dated Nov. 9, 2010.
PCT International Preliminary Report on Patentability, PCT/US2008/073964 filed Aug. 22, 2008, dated Feb. 24, 2010.
PCT International Preliminary Report on Patentability, PCT/US2009/035458 filed Feb. 27, 2009, dated Aug. 31, 2010.
PCT International Search Report and the Written Opinion, PCT/US2007/006824 filed Mar. 19, 2007, dated May 14, 2008.
PCT International Preliminary Report on Patentability, PCT/US2009/035463 filed Feb. 27, 2009, dated Aug. 31, 2010.
European Communication Pursuant to Article 94(3) EPC, Application No. 07810382.7, dated Dec. 8, 2010.

Chinese Office Action, Application No. 200780005821.2 dated Jan. 26, 2011.
PCT International Preliminary Report on Patentability, PCT/US2006/029889 filed Jul. 31, 2006, dated Feb. 5, 2008.
PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
European Search Report, Application No. 08798444.9-2402, PCT/US2008/073964, dated Dec. 16, 2010.
PCT International Preliminary Report on Patentability, PCT/US2007/009910 filed Apr. 24, 2007, dated Oct. 28, 2008.
PCT International Preliminary Report on Patentability, PCT/US2007/020215 filed Sep. 17, 2007, dated Mar. 24, 2009.
PCT International Preliminary Report on Patentability, PCT/US2007/023660 filed Nov. 1, 2007, dated May 5, 2009.
PCT International Preliminary Report on Patentability, PCT/US2008/007196 filed Jun. 9, 2008, dated Dec. 11, 2009.
PCT International Preliminary Report on Patentability, PCT/US2008/072081 filed Aug. 4, 2008, dated Feb. 9, 2010.
PCT International Preliminary Report on Patentability, PCT/US2009/035482 filed Feb. 27, 2009, dated Aug. 31, 2010.
European Search Reoprt, Application No. 08841700.1, dated Jan. 4, 2011.
PCT International Search Report and the Written Opinion, PCT/US2010/025173 filed Feb. 24, 2010, dated Jul. 6, 2010.
PCT International Preliminary Report on Patentability, PCT/US2007/015892 filed Jul. 12, 2007, dated Jan. 13, 2009.
PCT International Search Report and the Written Opinion, PCT/US2009/65072 filed Nov. 19, 2009, dated Mar. 3, 2010.
PCT International Preliminary Report on Patentability, PCT/US2009/035470 filed Feb. 27, 2009, dated Aug. 31, 2010.
PCT International Search Report and the Written Opinion, PCT/US2006/29889 filed Jul. 31, 2006, dated Jul. 10, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/15892 filed Jul. 12, 2007, dated Sep. 30, 2008.
PCT International Search Report and the Written Opinion, PCT/US2008/73964 filed Aug. 22, 2008, dated Dec. 24, 2008.
European Search Report, Application No. 08841700.1 dated Jun. 2, 2010.
PCT International Preliminary Report on Patentability, PCT/US2008/075565 filed Sep. 8, 2008, dated Mar. 9, 2010.
Chinese Office Action, Application No. 200680036598.3 dated Feb. 24, 2011.
Canadian Office Action, Application No. 2,617,581, dated Feb. 1, 2011.
European Communication Pursuant to Article 94(3) EPC, Application No. 07867402.5, dated Jan. 5, 2011.
PCT International Preliminary Report on Patentability, PCT/US2008/066870 filed Jun. 13, 2008, dated Dec. 17, 2009.
EP Search Report, Application No. 08782609.5 dated Oct. 28, 2010.
European Communication Pursuant to Article 94(3) EPC, Application No. 08767439.9, dated Mar. 15, 2011.
European Communication Pursuant to Article 94(3) EPC, Application No. 08768266.2, dated Apr. 18, 2011.
European Supplementary Search Report, Application No. 09715064.3 dated May 24, 2011.
European Communication Pursuant to Article 94(3) EPC, Application No. 07716208.9, dated Sep. 13, 2011,
Chinese Office Action, Application No. 200780040146.7 dated May 25, 2011.
European Seach Report, Application No. 09714868.8 dated Aug. 1, 2011.
PCT International Preliminary Report on Patentability, PCT/US2010/025173 filed Feb. 24, 2010, dated Sep. 9, 2011.
Australian Office Action, Application No. 2006291165 dated Aug. 23, 2011.
Chinese Office Action, Application No. 200680039776.8 dated Jun. 30, 2011.
PCT International Preliminary Report on Patentability, PCT/US2006/035100 filed Sep. 11, 2006, dated Mar. 18, 2008.
PCT International Preliminary Report on Patentability, PCT/US2009/065072 filed Nov. 19, 2009, dated Jun. 3, 2011.
PCT International Search Report and the Written Opinion, PCT/US2008/07196 filed Jun. 9, 2008, dated Nov. 19, 2008.
PCT International Preliminary Report on Patentability, PCT/US2008/001157 filed Jan. 29, 2008, dated Aug. 4, 2009.
PCT International Preliminary Report on Patentability, PCT/US2006/038824 filed Oct. 4, 2006, dated Apr. 9, 2008.
PCT International Preliminary Report on Patentability, PCT/US2007/006824 filed Mar. 19, 2007, dated Sep. 23, 2008.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Search Report and the Written Opinion, PCT/US2008/84821 filed Nov. 26, 2008, dated Feb. 17, 2009.
PCT International Search Report and the Written Opinion, PCT/US2006/38824 filed Oct. 4, 2006, dated Aug. 9, 2007.
PCT International Search Report and the Written Opinion, PCT/US2007/00024 filed Jan. 3, 2007, dated Nov. 5, 2007.
PCT International Search Report and the Written Opinion, PCT/US2007/09910 filed Apr. 24, 2007, dated Feb. 13, 2008.
PCT International Search Report and the Written Opinion, PCT/US2007/23660 filed Nov. 1, 2007, dated Sep. 16, 2008.
PCT International Search Report and the Written Opinion, PCT/US2007/20215 filed Sep. 17, 2007, dated Jul. 25, 2008.
Notice of Allowance and Fees Due in U.S. Appl. No. 12/298,221, filed Nov. 10, 2008, mailing date Nov. 30, 2009.
PCT International Search Report and the Written Opinion, PCT/US2008/05503 filed Apr. 29, 2008, dated Sep. 25, 2008.
Office Action issued in U.S. Appl. No. 12/293,471, filed Oct. 9, 2008, mailing date Jun. 8, 2010.
PCT International Search Report and the Written Opinion, PCT/US2006/35100 filed Sep. 11, 2006, dated Sep. 5, 2007.
PCT International Search Report and the Written Opinion, PCT/US2009/35470 filed Feb. 27, 2009, dated Jun. 16, 2009.
PCT International Search Report and the Written Opinion, PCT/US2008/71532 filed Jul. 30, 2008, dated Apr. 17, 2009.
PCT International Search Report and the Written Opinion, PCT/US2009/53586 filed Aug. 12, 2009, dated Oct. 28, 2009.
PCT International Search Report and the Written Opinion, PCT/US2009/46999 filed Jun. 11, 2009, dated Nov. 23, 2009.
PCT International Search Report and the Written Opinion, PCT/US2009/35482 filed Feb. 27, 2009, dated Jul. 17, 2009.
PCT International Search Report and the Written Opinion, PCT/US2009/35463 filed Feb. 27, 2009, dated Aug. 13, 2009.
PCT International Search Report and the Written Opinion, PCT/US2009/35458 filed Feb. 27, 2009, dated Jul. 28, 2009.
PCT International Search Report and the Written Opinion, PCT/US2008/81294 filed Oct. 27, 2008, dated Mar. 26, 2009.
PCT International Search Report and the Written Opinion, PCT/US2008/79482 filed Oct. 10, 2008, dated Dec. 22, 2008.
PCT International Search Report and the Written Opinion, PCT/US2008/75565 filed Sep. 8, 2008, dated Dec. 9, 2008.
PCT International Search Report and the Written Opinion, PCT/US2008/72081 filed Aug. 4, 2008, dated Jan. 14, 2009.
PCT International Search Report and the Written Opinion, PCT/US2008/01157 filed Jan. 29, 2008, dated Aug. 7, 2008.
European Search Report, Application No. 07753450.1 dated Jan. 12, 2009.
PCT International Search Report and the Written Opinion, PCT/US2009/38214 filed Mar. 25, 2009, dated Aug. 14, 2009.
Canadian Intellectual Property Office, Requisition by the Examiner, Application No. 2,635,616, Dated Feb. 21, 2011.
European Search Report, Application No. 06800599.0 dated Oct. 19, 2009.
European Search Report, Application No. 07717903.4 dated Oct. 23, 2009.

European Search Report, Application No. 07717734.3 dated Nov. 9, 2009.
European Search Report, Application No. 07716208.9 dated Nov. 10, 2009.
European Search Report, Application No. 07872618.9 dated Jul. 5, 2010.
European Search Report, Application No. 08767439.6 dated May 12, 2010.
European Search Report, Application No. 08796821.0 dated Aug. 4, 2010.
European Search Report, Application No. 07810382.7 dated Sep. 14, 2009.
European Search Report, Application No. 08768266.2 dated Jul. 1, 2010.
PCT International Search Report and the Written Opinion, PCT/US2007/006824 filed Mar. 19, 2007, dated Mar. 3, 2008.
European Search Report, Application No. 06825457.2 dated Sep. 16, 2009.
PCT International Preliminary Report on Patentability, PCT/US2008/005503 filed Apr. 29, 2008, dated Nov. 3, 2009.
European Search Report, Application No. 07867402.5 dated Mar. 16, 2010.
European Patent Application, EP 1795203 A2, Croce et al., Application No. 06010581.4, filed Feb. 7, 1997, published Jun. 13, 2007.
PCT International Search Report and the Written Opinion, PCT/US2008/66870 filed Jun. 13, 2008, dated Nov. 10, 2008.
Office Action issued in U.S. Appl. No. 12/373,358, filed Feb. 11, 2009, mailing date Aug. 20, 2010.
Office Action issued in U.S. Appl. No. 12/160,034, filed Jul. 3, 2008, mailing date Jun. 7, 2010.
Notice of Allowance and Fees Due in U.S. Appl. No. 12/160,064, filed Jul. 3, 2008, mailing date Nov. 20, 2009.
Office Action issued in U.S. Appl. No. 12/442,018, filed Mar. 27, 2009, mailing date Apr. 15, 2010.
Office Action issued in U.S. Appl. No. 12/083,067, filed Jun. 20, 2008, mailing date Jul. 8, 2010.
Office Action issued in U.S. Appl. No. 12/160,061, filed Jul. 3, 2008, mailing date Apr. 24, 2009.
Office Action issued in U.S. Appl. No. 12/160,061, filed Jul. 3, 2008, mailing date Oct. 30, 2009.
Office Action issued in U.S. Appl. No. 12/160,061, filed Jul. 3, 2008, mailing date Mar. 12, 2010.
Office Action issued in U.S. Appl. No. 12/160,064, filed Jul. 3, 2008, mailing date Aug. 10, 2009.
European Search Report, Application No. 06814375.9 dated Oct. 8, 2009.
Akahoshi, M. et al., "Myeloproliferative Disorders Terminating in Acute Megakaryoblastic Leukemia with Chromosome 3q26 Abnormality," Cancer, 1987, pp. 2654-2661, vol. 60.
Akao, Y. et al., "let-7 MicroRNA Functions as a Potential Growth Suppressor in Human Colon Cancer Cells," Biol. Pharm. Bull., May 2006, pp. 903-906, vol. 29, No. 5.
Alvarez-Secord, A. et al., "Maspin Expression in Epithelial Ovarian Cancer and Associations with Poor Prognosis: A Gynecologic Oncologic Oncology Group Study," Gynecologic Oncology, 2006, pp. 390-397, vol. 101.
Ambros, V. et al., "A Uniform System for MicroRNA Annotation," RNA, 2003, pp. 277-279, vol. 9.
Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.
Aqeilan, R. I. et al., "Targeted Deletion of WWOX Reveals a Tumor Suppressor Function," PNAS, Mar. 2007, pp. 3949-3954, vol. 104, No. 10.
Baira, E. et al., "Ultraconserved Elements: Genomics, Function and Disease," RNA Biology, Jul. 2008, pp. 132-134, vol. 5, No. 3.
Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.
Bartel, D. P., "MicroRNAs: Target Recognition and Regulatory Functions," Cell, Jan. 2009, pp. 215-233, vol. 136.

Bednarek, A. K. et al., "WWOX, the FRA16D Gene, Behaves as a Suppressor of Tumor Growth," Cancer Research, Nov. 2001, pp. 8068-8073, vol. 61.
Bejenaro, et al., "Ultraconserved Elements in the Human Genome," Electronic Suppl. Data, Science, 2004.
Bejerano, G. et al., "Ultraconserved Elements in the Human Genome," Science, May 2004, pp. 1321-1325, vol. 304.
Bell, D. A., "Origins and Molecular Pathology of Ovarian Cancer," Modern Pathology, 2005, pp. S19-S32, vol. 18.
Bichi, R. et al., "Human Chronic Lymphocytic Leukemia Modeled in Mouse by Targeted TCL1 Expression," PNAS, May 2002, pp. 6955-6960, vol. 99, No. 10.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.
Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.
Budhu, A. et al., "Identification of Metastasis-Related MicroRNAs in Hepatocellular Carcinoma," Hepatology, Mar. 2008, pp. 897-907, vol. 47, No. 3.
Caldas, C. et al., "Sizing Up miRNAs as Cancer Genes," Nature Medicine, Jul. 2005, pp. 712-714, vol. 11, No. 7.
Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.
Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.
Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.
Calin, G. A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Calin, G. A. et al., "MicroRNA Signatures in Human Cancers," Nature Reviews Cancer, Nov. 2006, pp. 857-866, vol. 6.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "Ultraconserved Regions Encoding ncRNAs are Altered in Human Leukemias and Carcinomas," Cancer Cell, Sep. 2007, pp. 215-229, vol. 12.
Cannistra, S.A., "Cancer of the Ovary," The New England Journal of Medicine, 2004, pp. 2519-2529, vol. 351, No. 25.
Castoldi, M. et al., "A Sensitive Array for MicroRNA Expression Profiling (miChip) Based on Locked Nucleic Acids (LNA)," RNA, 2006, pp. 913-920, vol. 12.
Chan, J. A. et al., "MicroRNA-21 is an Antiapoptotic Factor in Human Glioblastoma Cells," Cancer Research, Jul. 2005, pp. 6029-6033, vol. 65, No. 14.
Chang, N.-S. et al., "Molecular Mechanisms Underlying WOX1 Activation During Apoptotic and Stress Responses," Biochemical Pharmacology, 2003, pp. 1347-1354, vol. 66.
Chang, T.-C. et al., "Widespread MicroRNA Repression by Myc Contributes to Tumorigenesis," Nat Genet., Jan. 2008, pp. 43-50, vol. 40, No. 1.

Chen, C.-Z. et al., "MicroRNAs as Regulators of Mammalian Hematopoiesis," Seminars in Immunology,2005, pp. 155-165, vol. 17.

Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.

Chim, S.S.C. et al., "Detection and Characterization of Placental MicroRNAs in Maternal Plasma," Clinical Chemistry, 2008, pp. 482-490, vol. 54, No. 3.

Ciafre, S. A. et al., "Extensive Modulation of a Set of MicroRNAs in Primary Glioblastoma," Biochemical and Biophysical Research Communications, 2005, pp. 1351-1358, vol. 334.

Cimmino, A. et al., "miR-15 and miR-16 Induce Apoptosis by Targeting BCL2," PNAS, Sep. 2005, pp. 13944-13949, vol. 102, No. 39.

Cimmino, A. et al., Corrections to "miR-15 and miR-16 Induce Apoptosis by Targeting BCL2," PNAS, Feb. 2006, pp. 2464-2465, vol. 103, No. 7.

Costinean, S. et al., "Pre-B Cell Proliferation and Lymphoblastic Leukemia/ High-Grade Lymphoma in EµmiR155 Transgenic Mice," PNAS, May 2006, pp. 7024-7029, vol. 103, No. 18.

Croce, C. M. et al., "miRNAs, Cancer, and Stem Cell Division," Cell, 2005, pp. 6-7, vol. 36.

Croce, C. M. et al., "Role of FHIT in Human Cancer," Journal of Clinical Oncology, May 1999, pp. 1618-1624, vol. 17, No. 5.

Croce, C. M., "Causes and Consequences of MicroRNA Dysregulation in Cancer," Nature Reviews Genetics, Oct. 2009, pp. 704-714, vol. 10.

Croce, C. M., "Oncogenes and Cancer," The New England Journal of Medicine, Jan. 2008, pp. 502-511, vol. 358, No. 5.

Cui, S. et al., "MicroRNAs that Underlie Ovarian Cancer Development and Response to Chemotherapy," 98th AACR Annual Meeting, Apr. 14-18, 2007, Los Angeles, CA.

Dalmay, T. et al., "MicroRNAs and the Hallmarks of Cancer," Oncogene, 2006, pp. 6170-6175, vol. 25.

Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.

Davies, F. E. et al., "Insights into the Multistep Transformation of MGUS to Myeloma Using Microarray Expression Analysis," Blood, Dec. 2003, pp. 4504-4511, vol. 102, No. 13.

Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.

Dohner, H. et al., "Genomic Aberrations and Survival in Chronic Lymphocytic Leukemia," The New England Journal of Medicine, Dec. 2000, pp. 1910-1916, vol. 343, No. 26.

Druck, etal., "FHIT," Atlas of Genetics and Cytogenetics in Oncology and Haematology, 2007, pp. 171-178, vol. 2.

Eis, P. S. et al., "Accumulation of miR-155 and BIC RNA in Human B Cell Lymphomas," PNAS, Mar. 2005, pp. 3627-3632, vol. 102, No. 10.

Esquela-Kerscher, A. et al., "Oncomirs—MicroRNAs with a Role in Cancer," Nature Reviews:Cancer, Apr. 2006, pp. 259-269, vol. 6.

Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.

Fabbri, M. et al., "MicroRNAs," The Cancer Journal, Jan./Feb. 2008, pp. 1-6, vol. 14, No. 1.

Fabbri, M. et al., "WWOX Gene Restoration Prevents Lung Cancer Growth in Vitro and in Vivo," PNAS, Oct. 2005, pp. 15611-15616, vol. 102, No. 43.

Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.

Feng, G. et al., "Elevated Serum-Circulating RNA in Patients with Conventional Renal Cell Cancer," Anticancer Research, 2008, pp. 321-326, vol. 28.

Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.

Fong, Y. et al., "Muir-Torre-Like Syndrome in FHIT-Deficient Mice," PNAS, Apr. 2000, pp. 4742-4747, vol. 97, No. 9.

Ford, L.P., "A MicroRNA Expression Signature of Human Solid Tumors Defines Cancer Gene Targets," Leukemia Research, 2006, pp. 511-513, vol. 30.

Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.

Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.

Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.

Garzon, R. et al., "MicroRNA Expression and Function in Cancer," Trends in Molecular Medicine, Oct. 2006, pp. 580-587, vol. 12, No. 12.

Garzon, R. et al., "MicroRNA Fingerprints During Human Megakaryocytopoiesis," PNAS, Mar. 2006, pp. 5078-5083, vol. 103, No. 13.

Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.

Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.

Godlewski, J. et al., "Targeting of the Bmi-1 Oncogene/Stem Cell Renewal Factor by MicroRNA-128 Inhibits Giloma Proliferation and Self-Renewal," Cancer Research, Nov. 2008, pp. 9125-9130, vol. 68, No. 22.

Gourley, C. et al., "WWOX Gene Expression Abolishes Ovarian Cancer Tumorigenicity in Vivo and Decreases Attachment to Fibronectin via Integrin α3," Cancer Research, Jun. 2009, pp. 4835-4842, vol. 69, No. 11.

Griffiths-Jones, S. et al., "miRBase: MicroRNA Sequences, Targets and Gene Nomenclature," Nucleic Acids Research, 2006, pp. D140-D144, vol. 34.

Griffths-Jones, S. et al., "miRBase: Tools for MicroRNA Genomics," Nucleic Acids Research, 2008, pp. D154-D157, vol. 36.

Griffths-Jones, S., "The MicroRNA Registry," Nucleic Acids Research, 2004, pp. D109-D111, vol. 32.

Guimaraes-Sternberg, C. et al., "MicroRNA Modulation of Megakaryoblast Fate Involves Cholinergic Signaling," Leukemia Research, 2006, pp. 583-595, vol. 30.

Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.

Havelange, V. et al., "MicroRNAs: New Players in Acute Myeloid Leukemia," British Journal of Cancer, 2009, pp. 743-748, vol. 101.

Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.

He, L. et al., "A MicroRNA Polycistron as a Potential Human Oncogene," Nature, Jun. 2005, pp. 828-833, vol. 435.

He, X. et al., "MicroRNA and Esophageal Carcinoma," Journal of Nanjing Medical University, 2007, pp. 201-206, vol. 21, No. 4.

Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.

Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.

Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.

Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.

Iliopoulos, D. et al., "Inhibition of Breast Cancer Growth InVitro and in Vivo: Effect of Restoration of WWOX Expression," Clin. Cancer Research, Jan. 2007, pp. 268-274, vol. 13, No. 1.

Iorio, M. V. et al., "MicroRNA Gene Expression Deregulation in Human Breast Cancer," Cancer Research, Aug. 2005, pp. 7065-7070, vol. 65, No. 16.

Iorio, M. V. et al., "MicroRNA Signatures in Human Ovarian Cancer," Cancer Research, Sep. 2007, pp. 8699-8707, vol. 67, No. 18.

Ishii, H. et al., "Effect of Adenoviral Transduction of the Fragile Histidine Triad Gene into Esophageal Cancer Cells," Cancer Research, Feb. 2001, pp. 1578-1584, vol. 61.

Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.

Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.

Jacobs, I.J. et al., "Progress and Challenges in Screening for Early Detection of Ovarian Cancer," Molecular & Cellular Proteomics, 2004, pp. 355-366, vol. 3.

Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.

Jemal, A. et al., "Cancer Statistics, 2008," CA Cancer J. Clin., 2008, pp. 71-96, vol. 58, No. 2.

Ji, J. et al., "MicroRNA Expression, Survival, and Response to Interferon in Liver Cancer," The New England Journal of Medicine, Oct. 2009, pp. 1437-1447, vol. 361, No. 15.

Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.

Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.

Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.

Jiang, J. et al., "Real-Time Expression Profiling of MicroRNA Precursors in Human Cancer Cell Lines," Nucleic Acids Research, 2005, pp. 5394-5403, vol. 33, No. 17.

John, B. et al., "Human MicroRNA Targets," PLOS Biology, Nov. 2004, pp. 1862-1879, vol. 2, Issue 11.

Johnson, S. M. et al., "RAS is Regulated by the let-7 MicroRNA Family," Cell, Mar. 2005, pp. 635-647, vol. 120.

Johnson, S. M. et al., "RAS is Regulated by the let-7 MicroRNA Family," Supplemental Data, Cell, Mar. 2005, pp. 635-647, vol. 120.

Kawasaki, H. et al., "MicroRNA-196 Inhibits HOXB8 Expression in Myeloid Differentiation of HL60 Cells," Nucleic Acids Symposium Series, 2004, pp. 211-212, No. 48.

Kelly, L.M. et al., "CT53518, A Novel Selective FLT3 Antagonist for the Treatment of Acute Myelogenous Leukemia (AML)," Cancer Cell, Jun. 2002, pp. 421-432, vol. 1.

Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.

Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, 2007 Apr. 14-18, Los Angeles, CA: AACR, 2007, 2 pages, Abstract No. 1780.

Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.

Kozomara, A. et al., "miRBase: Integrating MicroRNA Annotation and Deep-Sequencing Data," Nucleic Acids Research, 2011, pp. D152-D157, vol. 39.

Krek, A. et al., "Combinatorial MicroRNA Target Predictions," Nature Genetics, May 2005, pp. 495-500, vol. 37, No. 5.

Kulshreshtha, R. et al., "A MicroRNA Signature of Hypoxia," Molecular and Cellular Biology, Mar. 2007, pp. 1859-1867, vol. 27, No. 5.

Kuroki, et al., "Genetic Alterations of the Tumor Suppressor Gene WWOX in Esophageal Squamous Cell Carcinoma," Cancer Research, Apr. 2002, pp. 2258-2260, vol. 62.

Kutay, H. et al., "Downregulation of miR-122 in the Rodent and Human Hepatocellular Carcinomas," Journal of Cellular Biochemistry, 2006, pp. 671-678, vol. 99.

Lagos-Quintana, M. et al., "Identification of Tissue-Specific MicroRNAs from Mouse," Current Biology, Apr. 2002, pp. 735-739, vol. 12.

Lagos-Quintana, M. et al., "New MicroRNAs From Mouse to Human," RNA, 2003, pp. 175-179, vol. 9, No. 2.

Landgraf, P. et al., "A Mammalian MicroRNA Expression Atlas Based on Small RNA Library Sequencing," Cell, Jun. 2007, pp. 1401-1414, vol. 129.

Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.

Lanza, G. et al., "mRNA/microRNA Gene Expression Profile in Microsatellite Unstable Colorectal Cancer," Molecular Cancer, 2007, pp. 1-11, vol. 6, No. 54.

Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.

Lee, E. J. et al., "Expression Profiling Identifies MicroRNA Signature in Pancreatic Cancer," Int. J. Cancer, 2006, pp. 1046-1054, vol. 120.

Lewis, B. P. et al., "Prediction of Mammalian MicroRNA Targets," Cell, Dec. 2003, pp. 787-798, vol. 115.

Li, S.-C. et al., "Bioinformatic Discovery of MicroRNA Precursors from Human ESTs and Introns," BMC Genomics, 2006, vol. 7.

Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.

Lin, R.-K. et al., "Alteration of DNA Methyltransferases Contributes to 5'CpG Methylation and Poor Prognosis in Lung Cancer," Lung Cancer, 2007, pp. 205-213, vol. 55.

Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.

Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.

Lu, J. et al., "MicroRNA Expression Profiles Classify Human Cancers," Nature, Jun. 2005, pp. 834-838, vol. 435, Supplementary Information.

Lu, J. et al., "MicroRNA Expression Profiles Classify Human Cancers," Nature, Jun. 2005, pp. 834-838, vol. 435.

Lujambio, A. et al., "A MicroRNA DNA Methylation Signature for Human Cancer Metastasis," PNAS, Sep. 2008, pp. 13556-13561, vol. 105, No. 36.

Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.

Mack, G. S., "MicroRNA Gets Down to Business," Nature Biotechnology, Jun. 2007, pp. 631-638, vol. 25, No. 6.

Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.

Marcucci, et al., "MicroRNA Expression in Cytogenetically Normal Acute Myeloid Leukemia," NEJM, May 2008, pp. 1919-1928, vol. 358, No. 18.

Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.

McManus, M. T., "MicroRNAs and Cancer," Seminars in Cancer Biology, 2003, pp. 253-258, vol. 13.

Medina, P.P. et al., "OncomiR Addiction in an In Vivo Model of MicroRNA-21-Induced Pre-B-Cell Lymphoma," Nature Letters, Sep. 2010, pp. 86-91, vol. 467.

Medina, P.P., "OncomiR Addicton in an in vivo Model of MicroRNA-21-Induced Pre-B-Cell Lymphoma," Supplementary Information, Sep. 2010, p. 1-22.

Megraw, M. et al., "miRGen: A Database for the Study of Animal MicroRNA Genomic Organization and Function," Nucleic Acids Research, 2007, pp. D149-D155, vol. 35.

Mendell, J.T., "miRiad Roles for the miR-17-92 Cluster in Development and Disease," Cell, 2008, pp. 217-222.

Meng, F. et al., "MicroRNA-21 Regulates Expression of the PTEN Tumor Suppressor Gene in Human Hepatocellular Cancer," Gastroenterology, 2007, pp. 647-658, vol. 133.

Meng, F. et al., "Involvement of Human MicroRNA in Growth and Response to Chemotherapy in Human Cholangiocarcinoma Cell Lines," Gastroenterology, 2006, pp. 2113-2129, vol. 130.

Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.

Michael, M. Z. et al., "Reduced Accumulation of Specific MicroRNAs in Colorectal Neoplasia," Molecular Cancer Research, Oct. 2003, pp. 882-891, vol. 1.

Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.

Mitchell, P. S. et al., "Circulating MicroRNAs as Stable Blood-Based Markers for Cancer Detection," PNAS, Jul. 2008, pp. 10513-10518, vol. 105, No. 30.

Mitrovic, T. et al., "Cancer Gene Therapy," Arch. Oncology, 2005, pp. 23-26, vol. 13, No. 1.

Mountzios, G. et al., "Mechanisms of Disease: Signal Transduction in Lung Carcinogenesis-A Comparison of Smokers and Never-Smokers," Nature Clinical Practice Oncology, Oct. 2008, pp. 610-618, vol. 5, No. 10.

Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.

Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.

Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.

Nam, E.J. et al., "MicroRNA Expression Profiles in Serous Ovarian Carcinoma," Clinical Cancer Research, 2008, pp. 2690-2695, vol. 14, No. 9.

Negrini, M. et al., "MicroRNAs in Human Cancer: From Research to Therapy," Journal of Cell Science, Apr. 2007, pp. 1833-1840, vol. 120.

Nicoloso, M.S. et al., "MicroRNAs—The Micro Steering Wheel of Tumour Metastases," Nature Reviews: Cancer, Apr. 2009, pp. 293-302, vol. 9.

Nurden, A.T., "Qualitative Disorders of Platelets and Megakaryocytes," Journal of Thrombosis and Haemostasis, 2005, vol. 3, pp. 1773-1782.

Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.

Palamarchuk, A. et al., "Akt Phosphorylates TCl1 Oncoprotein and Inhibits Its Repressor Activity," Cancer Research, Jun. 2005, pp. 4515-4519, vol. 65, No. 11.

Pawelczyk, T. et al., "Expression in *Escherichia Coli* and Simple Purification of Human Fhit Protein," Protein Expr. Purlf., Apr. 2000, pp. 320-326, vol. 18, No. 3.

Pedersen, I. M. et al., "Interferon Modulation of Cellular MicroRNAs as an Antiviral Mechanism," Nature, Oct. 2007, pp. 919-922, vol. 449.

Pekarsky, Y. et al., "Animal Models for Chronic Lymphocytic Leumekia," Journal of Cellular Biochemistry, 2007, pp. 1109-1118, vol. 100.

Pekarsky, Y. et al., "Tcl1 Enhances Akt Kinase Activity and Mediates Its Nuclear Translocation," PNAS, Mar. 2000, pp. 3028-3033, vol. 97, No. 7.

Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.

Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.

Petrocca, F. et al., "MicroRNAs Deregulation in Gastric Cancer," PNAS, Apr. 2006, p. 1338, vol. 47, Abstract # 5690.

Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.

Pichiorri, F. et al., "MicroRNAs Regulate Critical Genes Associated with Multiple Myeloma Pathogenesis," PNAS, Sep. 2008, pp. 12885-12890, vol. 105, No. 35.

Pineau, P. et al., "miR-221 Overexpression Contributes to Liver Tumorigenesis," PNAS, Jan. 2010, pp. 264-269, vol. 107, No. 1.

Porkka, K.P. et al., "MicroRNA Expression Profiling in Prostate Cancer," Cancer Research, 2007, pp. 6130-6135, vol. 67, No. 13.

Prueitt, R. L. et al., "Expression of MicroRNAs and Protein-Coding Genes Associated with Perineural Invasion in Prostate Cancer," The Prostate, 2008, pp. 1152-1164, vol. 68.

Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.

Qin, H. R. et al., "A Role for the WWOX Gene in Prostate Cancer," Cancer Research, Jul. 2006, pp. 6477-6481, vol. 66, No. 13.

Ramkissoon, S. H, et al., "Hematopoietic-Specific MicroRNA Expression in Human Cells," Leukemia Research, 2006, pp. 643-647, vol. 30.

Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.

Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.

Saini, H. K. et al., "Annotation of Mammalian Primary MicroRNAs," BMC Genomics, 2008, vol. 9.

Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.

Santanam, U. et al., "Chronic Lymphocytic Leukemia Modeled in Mouse by Targeted miR-29 Expression," PNAS, Jul. 2010, pp. 12210-12215, vol. 107, No. 27.

Sasaki, Y.T.F. et al., "Coordinated Expression of ncRNAs and HOX mRNAs in the Human HOXA Locus," Biochemical and Biophysical Communications, 2007, pp. 724-730, vol. 357.

Schagen, F. et al., "Genetic Targeting of Adenovirus Vectors Using a Reovirus Sigma1-Based Attachment Protein," Molecular Therapy, May 2006, pp. 997-1005, vol. 13, No. 5.

Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.

Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.

Schmittgen, T. D. et al., "A High-Throughput Method to Monitor the Expression of MicroRNA Precursors," Nucleic Acids Research, Feb. 2004, vol. 32, No. 4.

Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.

Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.

Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.

Seth, P., "Vector-Mediated Cancer Gene Therapy," Cancer Biology & Therapy, May 2005, pp. 512-517, vol. 4, Issue 5.

Sevinsky, J. R. et al., "Extracellular Signal-Regulated Kinase Induces the Megakaryocyte GPllb/CD41 Gene Through MafB/Kreisler," Molecular and Cellular Biology, May 2004, pp. 4534-4545, vol. 24, No. 10.

Sharma, S. et al., "Development of Inhalational Agents for Oncologic Use," Journal of Clinical Oncology, Mar. 2001, Abstract, vol. 19, Issue 6.

Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.

Slack, F.J., "Big Roles for Small RNAs," Nature, Feb. 2010, p. 616, vol. 463.

Suarez-Saiz, F.J. et al., "MicroRNA Expression Profiling in Acute Myelogenous Leukemia," Canada Blood, Nov. 2004, Abstract #1131, p. 320A.

Taccioli, C. et al., "Ucbase & miRfunc: A Database of Ultraconserved Sequences and MicroRNA Function," Nucleic Acids Research, 2009, pp. D41-D48, vol. 37.

Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.

Tang, X. et al., "A Simple Array Platform for MicroRNA Analysis and Its Application in Mouse Tissues," RNA, Aug. 2007, pp. 1-20, vol. 13.

Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.

Thomson, J. M. et al., "A Custom Microarray Platform for Analysis of MicroRNA Gene Expression," Nature Methods, Oct. 2004, pp. 1-7, vol. 1, No. 1.

Thomson, M., Supplementary data for "A Custon Microarray Platform for Analysis of MicroRNA Gene Expression," Nature Methods, Oct. 2004, pp. 47-53, vol. 1, No. 1.

Thorgeirsson, S. S. et al., "Functional Genomics of Hepatocellular Carcinoma," Hepatology, Feb. 2006, pp. S145-S150, vol. 43, No. 2, Suppl. 1.

Tilt, E. et al., "Expression and Function of Micro RNAs in Immune Cells During Normal or Disease State," International Journal of Medicine Sciences, 2008, pp. 73-79, vol. 5, No. 2.

Tockman, M. S. et al., "Considerations in Bringing a Cancer Biomarker to Clinical Application," Cancer Research, May 1992, pp. 2711s-2718s, vol. 52.

Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.

Tricoli, J. V. et al., "MicroRNA: Potential for Cancer Detection, Diagnosis, and Prognosis," Cancer Research, May 2007, pp. 4553-4555, vol. 67, No. 10.

Ueda, T. et al., "Relation Between MicroRNA Expression and Progression and Prognosis of Gastric Cancer: A MicroRNA Expression Analysis," Published Online; www.thelancet.com/oncology, Dec. 2009, D01:10.1016/S1470-2045(09)70343-2.

Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.

Valeri, N. et al., "Epigenetics, miRNAs, and Human Cancer: A New Chapter in Human Gene Regulation," Mamm Genome, Aug. 2009, pp. 573-580, vol. 20.

Valeri, N. et al., "Modulation of Mismatch Repair and Genomic Stability by miR-155," PNAS, Apr. 2010, pp. 6982-6987, vol. 107, No. 15.

Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.

Verschuur, A.C., "Acute Megakaryoblastic Leukemia," May 2004, pp. 1-5, Retrieved from the Internet: URL: http://www.orpga.net/data/patho/GB/uk-AMLM7.pdf.

Virgilio, L. et al., "Identification of the TCL1 Gene Involved in T-Call Malignancies," Proc. Natl. Acad. Sci., Dec. 1994, pp. 12530-12534, vol. 91.

Visone, R. et al., "MiRNAs and Cancer," The American Journal of Pathology, Apr. 2009, pp. 1131-1138, vol. 174, No. 4.

Volinia, et al., "Reprogramming of MirRNA Networks in Cancer and Leukemia," Genome Research, 2010, pp. 589-599, vol. 20.

Volinia, S. et al., "A MicroRNA Expression Signature of Human Solid Tumors Defines Cancer Gene Targets," PNAS, Feb. 2006, pp. 2257-2261, vol. 103, No. 7.

Wang, E. et al., "Ontogeny and Oncogenesis Balance the Transcriptional Profile of Renal Cell Cancer," Cancer Research, Oct. 2004, pp. 7279-7287, vol. 64.

Wang, X. et al., "Association Between CpG Island Methylation of the WWOX Gene and Its Expression in Breast Cancers," Tumor Biology, Feb. 2009, pp. 8-14, vol. 30.

Weidhaas, J., "Using MicroRNAs to Understand Cancer Biology," Published Online Dec. 21, 2009, DOI: 10.1016/S1470-2045(09)70386-9.

Wijermans, P.W., "Low Dose Azanucleosidesfor High Risk (s) MDS and AML," Haematologica Reports,Nov. 2006, pp. 74-76. vol. 2, Issue, 15.

Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.

Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.

Yanaihara, N. et al., "Unique MicroRNA Molecular Profiles in Lung Cancer Diagnosis and Prognosis," Cancer Cell, Mar. 2006, pp. 189-198, vol. 9.

Yang, J. et al., "Analysis of Sequence Variations in 59 MicroRNAs in Hepatocellular Carcinomas," Mutation Research, Aug. 2008, pp. 205-209, vol. 638.

Yendamuri, S. et al., "WW Domain Containing Oxidoreductase Gene Expression is Altered in Non-Small Cell Lung Cancer," Cancer Research, Feb. 2003, pp. 878-881, vol. 63.

Yoon, S. et al., "Prediction of Regulatory Modules Comprising MicroRNAs and Target Genes," Bioinformatics Genes and Genomes, 2005. Pages ii93-ii100, vol. 21, Suppl. 2.

Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemistry, Jul. 2004, pp. 41377-41383, vol. 279, No. 40.

Zawacka-Pankau, J. et al., "Expression and Simple, One-Step Purification of Fragile Histidine Triad (Fhit) Tumor Suppressor Mutant Forms in *Escherichia Coli* and their Interaction with Protoporphyrin IX," Biotechnology Letters, Jun. 2007, pp. 877-883, vol. 29, No. 6.

Zeng, Y. et al., "Recognition and Cleavage of Primary MicroRNA Precursors by the Nuclear Processing Enzyme Drosha," The EMBO Journal, 2005, pp. 138-148, vol. 24.

Zhang, L. et al., "Genomic and Epigenetic Alterations Deregulate MicroRNA Expression in Human Epithelial Ovarian Cancer," PNAS, May 2008, pp. 7004-7009, vol. 105, No. 19.

Zhang, L. et al., "MicroRNAs Exhibit High Frequency Genomic Alterations in Human Cancer," PNAS, Jun. 2006, pp. 9136-9141, vol. 103, No. 24.

Zhang, L. et al., Supporting Information, PNAS 2008, pp. 1-11.

Zhang, Z. et al., "Three Biomarkers Identified from Serum Proteomic Analysis for the Detection of Early Stage Ovarian Cancer," Cancer Research, Aug. 2004, pp. 5882-5890, vol. 64.

Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.

* cited by examiner

Nucleotide Sequence of Human Genomic fragment encoding microRNA-191
[SEQ ID NO.: 17], CTGGACAGCGGGCAACGGAATCCCAAAAGCAGCTGTTGTCTCCAGAGCATT
CCAGCTGCGCTTGGATTTCGTCCCTGCTCTCCTGCCTGAGCAGCGCCCTG
GCCCAGATGGGGTGCCCCTGACCCCAGACATACTTTACTGAGCTGCTTGG
GTCTCAGTTCCTCTCAGTTGCGCCCTCA Nucleotide Sequence of Human Genomic fragment encoding microRNA-155
[SEQ ID NO.: 18], ATGCCTCATCCTCTGAGTGCTGAAGGCTTGCTGTAGGCTGTATGCTGTTAAT
GCTAATCGTGATAGGGGTTTTTGCCTCCAACTGACTCCTACATATTAGCATT
AACAGTGTATGATGCCTGTTACTAGCATTCACATGGAACAAATTGCTGCCGT
GGGAG Nucleotide Sequence of Human Genomic fragment encoding microRNA-23a
[SEQ ID NO.: 19], TGATCAAAGGAAGCATCTGGGGACCTGGAGGGGAGGTGTCCCCAAATCTC
ATTACCTCCTTTGCTCTCTCTCTCTTTCTCCCTCCAGGTGCCAGCCTCTGGC
CCCGCCCGGTGCCCCCCTCACCCCTGTGCCACGGCCGGCTGGGGTTCCTG
GGGATGGGATTTGCTTCCTGTCACAAATCACATTGCCAGGGATTTCCAACCG
ACCCTGAGCTCTGCCACCGAGGATGCTG Nucleotide Sequence of Human Genomic fragment encoding microRNA-27a
[SEQ ID NO.: 20], CAGAGAGGCCCCGAAGCCTGTGCCTGGCCTGAGGAGCAGGGCTTAGCTGC
TTGTGAGCAGGGTCCACACCAAGTCGTGTTCACAGTGGCTAAGTTCCGCCC
CCCAGGCCCTCACCTCCTCTGGCCTTGCCGCCTGT

Figure 4E miR-191 probe (208 nt)

```
         5': 35 nt              ↓
                               ca     c  aa      uu  -  c
T7GGGCGAATTCGAGCTCGGTACCCcuggacagcggg   acggaaucc aa  gсagсug  gu cu c
                                      ||||||||| ||  ||||||  || || |
guagaccgggucccgcgacgaguccguccucucgucc   ugcuuaagg uu  сguсgaс  ua ga a
g                                    ↑ cc      -  сg      сu  с  g
g                                             hairpin: 64 nt
gtgcccctgacccccagacatactttactgagctg             (mature 191/191*: 22 nt)
                                 c
                                 u
gggacucccgcguagacucuccuugacucuggggu
↑
BamHI        3' : 109 nt
```

|              | RPA     | In vitro cleavage with Drosha |
|--------------|---------|-------------------------------|
| pri-miR      | 182 nt  | as uncleaved 208 nt           |
| hairpin      | 64 nt   | 64 nt                         |
| upstream (5')| 12 nt   | 35 nt                         |
| downstream (3')| 106 nt| 109 nt                        |

Figure 7A miR-23a probe (108 nt)

```
                              GAATTCtgatcaa
aggaagcatctgggacctggagggaggtgtccccaaatctca
ttacctcctttgctctctctctctttctccoctccaggtgccag
cctctggcccgcccggtgccccoctcaccoctgtgccacggcc|NaeI
                                              g    g       cauc
                            ggcuggggg  uacccagg gaug gauuug   c
                            |||| ||||||| |||| ||||||         u
SP6  GAATTTTAAAgacguaggagcuaccgucucgagucccagccaauuuu agggacc uuac cuaaac     u
                                              u    g    a       acuug
```

Figure 8A miR-27a probe (122 nt)

```
                    GAATTCcagagagcccccgaagctgtgcctggcc|Bsu36I
                                      a  a  a       ug  u       g  u cac
                                   ug gg gc gggcuaagc  cu gugagca gg c   a
                                   || || || |||||||||  || |||||||| || |  |
SP6  GAATTTTAAAtguccgccgguaccggucaccuccacuccggacccccgac  cc  cg cuuggaucg  ga caccuga cu g   c
                                   c  c  c       gu  -       g  - aac
```

Figure 8B

```
                        SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgcctcatc ctctgagtgc t                                             21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcccacggc agcaatttgt t                                             21

<210> SEQ ID NO 3
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
aagaaaagca gaccuacucc a                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
aagaaaagga aaugacccat t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtagctgcca ctaccacaga t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agccagagtc agatgctcag t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tacaagctac gtagcgcgag a                                              21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
actcggcctc ctaagactga gg                                             22
```

```
<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gttccctcta gactccgttt ca                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtcactacc attgcagccc ta                                              22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgagctcctt cctttcaaca g                                               21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gttgaacatc ccagtgacca g                                               21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tctaggtatc tctgcctctc ca                                              22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agcatcctcg gtggcagagc tca                                             23

<210> SEQ ID NO 15
<211> LENGTH: 23
```

-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgagctctgc caccgaggat gct                                              23

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acaggcggca aggccagagg a                                                21

<210> SEQ ID NO 17
<211> LENGTH: 181
<212> TYPE: DNA
<213> ORGANISM: Homo sapiens

<400> SEQUENCE: 17
ctggacagcg ggcaacggaa tcccaaaagc agctgttgtc tccagagcat tccagctgcg      60
cttggatttc gtcccctgct ctcctgcctg agcagcgccc tggcccagat ggggtgcccc     120 tgaccccccag acatacttta ctgagctgct tgggtctcag ttcctctcag ttgcgccctc    180
a                                                                    181

<210> SEQ ID NO 18
<211> LENGTH: 161
<212> TYPE: DNA
<213> ORGANISM: Homo sapiens

<400> SEQUENCE: 18
atgcctcatc ctctgagtgc tgaaggcttg ctgtaggctg tatgctgtta atgctaatcg      60
tgataggggt ttttgcctcc aactgactcc tacatattag cattaacagt gtatgatgcc    120
tgttactagc attcacatgg aacaaattgc tgccgtggga g                         161

<210> SEQ ID NO 19
<211> LENGTH: 233
<212> TYPE: DNA
<213> ORGANISM: Homo sapiens

<400> SEQUENCE: 19
tgatcaaagg aagcatctgg ggacctggag gggaggtgtc cccaaatctc attacctcct      60
ttgctctctc tctctttctc ccctccaggt gccagcctct ggccccgccc ggtgcccccc    120 tcaccccctgt gccacggccg gctggggttc ctggggatgg gatttgcttc ctgtcacaaa   180
tcacattgcc agggatttcc aaccgaccct gagctctgcc accgaggatg ctg           233

<210> SEQ ID NO 20
<211> LENGTH: 136
<212> TYPE: DNA
<213> ORGANISM: Homo sapiens

<400> SEQUENCE: 20
cagagaggcc ccgaagcctg tgcctggcct gaggagcagg gcttagctgc ttgtgagcag      60
ggtccacacc aagtcgtgtt cacagtggct aagttccgcc ccccaggccc tcacctcctc    120

```
tggccttgcc gcctgt                                                       136

<210> SEQ ID NO 21
<211> LENGTH: 208
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 21
gggcgaauuc gagcucggua ccccuggaca gcgggcaacg gaaucccaaa agcagcuguu        60
gucuccagag cauuccagcu gcgcuuggau uucguccccu gcucuccugc cugagcagcg       120
cccuggccca gaugggugc ccctgaccc cagacatact ttactgagct gcuugggucu        180 caguccucu caguugcgcc cucagggg                                          208

<210> SEQ ID NO 22
<211> LENGTH: 187
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 22
gggcgaauuc caugccucau ccucugagug cugaaggcuu gcuguaggcu guaugcuguu        60
aaugcuaauc gugauagggg uuuuugccuc caacugacuc cuacauauua gcauuaacag       120
uguaugaugc cuguuacuag cauucacaug gaacaaauug cugccguggg agcaagcuuc       180
uuaugag                                                                187

<210> SEQ ID NO 23
<211> LENGTH: 255
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
<223> OTHER INFORMATION: Description of Artificial Sequence: Synthetic
      probe

<400> SEQUENCE: 23
gaattcctga tcaaaggaag catctgggga cctggagggg aggtgtcccc aaatctcatt        60
acctcctttg ctctctctct ctttctcccc tccaggtgcc agcctctggc cccgccggt       120 gcccccctca cccctgtgcc acggccggcu ggggggccug gggaugggau uugcuuccug       180
ucacaaauca cauugccagg gauuuccaac cgacccugag cucugccacc gaggaugcug       240
caagcuucuu augag                                                       255

<210> SEQ ID NO 24
<211> LENGTH: 165
<212> TYPE: DNA
<213> ORGANISM: Artificial Sequence
<220> FEATURE:
<223> OTHER INFORMATION: Description of Combined DNA/RNA Molecule:
      Synthetic probe
<220> FEATURE:
```

-continued

```
<223> OTHER INFORMATION: Description of Artificial Sequence: Synthetic
      probe

<400> SEQUENCE: 24
gaattcccag agaggccccg aagcctgtgc ctggccuggg gcagggacuu aagccuguug         60
gagcuaggcg ucacaccaag ucguguucac aguggcuaag uuccgccccc cagcccccag        120
gcccucaccu ccucuggccu ugccgccugt caagcttctt atgag                        165
```

METHOD FOR DIAGNOSING ACUTE LYMPHOMIC LEUKEMIA (ALL) USING MIR-221

CROSS-REFERENCE TO RELATED APPLICATIONS

The present application is a divisional of U.S. patent application Ser. No. 12/664,531, having a 35 U.S.C. §371(c) filing date of Jan. 8, 2010, now U.S. Pat. No. 8,053,186, issued on Nov. 8, 2011, which is a 35 U.S.C. §371 National Stage patent application of International patent application PCT/US2008/066870, filed on Jun. 13, 2008, which claims priority to U.S. provisional patent application Ser. No. 60/934,707, filed on Jun. 15, 2007, the contents of which are hereby incorporated by reference in their entirety.

GOVERNMENT SUPPORT

The invention made with government support under Grant No. R01 CA128609, awarded by the National Cancer Institute. The Government has certain rights in the invention.

FIELD OF THE INVENTION

The present invention provides compositions and methods for modulation of small non-coding RNAs, particularly pri-miRNAs. In particular, this invention relates to compounds, particularly oligomeric compounds, which, in some embodiments, hybridize with or sterically interfere with nucleic acid molecules comprising or encoding small non-coding RNA targets, including pri-miRNAs.

SEQUENCE LISTING

The patent application contains a "Sequence Listing" section. A copy of the "Sequence Listing" is available in electronic form from the USPTO web site (seqdata.uspto.gov/sequence). A paper copy of the sequence listing and a computer-readable form of the sequence listing are herein incorporated by reference. An electronic copy of the "Sequence Listing" will also be available from the USPTO upon request and payment of the fee set forth in 37 CFR 1.19(b)(3). The ASCII copy, created on Jul. 23, 2008, is named 604_29185_SEQ_LIST_11011.txt, and is 8 KB in size.

BACKGROUND OF THE INVENTION

Acute leukemia is a rapidly progressive malignant disease of the bone marrow and blood that results in the accumulation of immature, functionless cells, called blast cells, in the marrow and blood. The accumulation of blast cells in the marrow blocks normal blood cell development. As a result, red cells, white cells and platelets are not produced in sufficient numbers. When the disease originates in a marrow lymphocyte progenitor cell, it results in acute lymphoblastic leukemia (ALL) and when the disease originates in a myeloid progenitor, it results in acute myelogenous leukemia (AML).

ALL is a rapidly progressive cancer that starts by the malignant transformation of a marrow lymphocyte. ALL is the most common type of childhood leukemia, with 3,000 new cases per year in all age groups. The transformed, now malignant, cell multiplies and accumulates in the marrow as leukemic lymphoblasts. The lymphoblasts block normal blood cell-formation in the marrow, resulting in insufficient production of red cells, white cells and platelets.

High-grade lymphomas, also known as aggressive lymphoma, include several subtypes of lymphoma that progress relatively rapidly if untreated. These subtypes include, e.g., AIDS-associated lymphoma, anaplastic large cell lymphoma, Burkitt's lymphoma, diffuse large cell lymphoma, immunoblastic lymphoma, lymphoblastic lymphoma and small non-cleaved cell lymphomas. Compared to diffuse large B-cell lymphomas, high-grade lymphomas behave more aggressively, require more intensive chemotherapy, and occur more often in children. Because rapidly dividing cells are more sensitive to anti-cancer agents and because the young patients usually lack other health problems, some of these lymphomas show a dramatic response to therapy. Acute lymphoblastic leukemia and high-grade lymphoma are the most common leukemias and lymphomas in children. These diseases are, for the most part, polyclonal, suggesting that only a few genetic changes are sufficient to induce malignancy.

ALL-1, also termed MLL has been cloned from chromosome band 11q23, recurrent site involved in multiple chromosome abnormalities associated with both acute lymphoblastic (ALL) and acute myeloblastic (AML) leukemia (1, 2). The chromosome translocation results in the fusion of the ALL1 gene with one of more than 50 different partner genes and the production of leukemogenic proteins composed of the N-terminal All1 sequence and a portion of the partner protein encoded by the segment of the gene positioned 3' to the breakpoint (ibid). The most prevalent ALL1 rearrangement in ALL is the ALL1/AF4 chimeric gene resulting from the t(4; 11) chromosome translocation. This rearrangement is associated with very poor prognosis in infants and adults (3). The molecular pathways deregulated by the All1 fusion protein, which bring about the aggressiveness of the disease are still largely unknown.

miRNAs are short 20-22 nucleotide RNA that negatively regulate the gene expression at the post-transcriptional level by base pairing to the 3' untranslated region of target messenger RNAs. More than 400 miRNAs have been identified in human and they are evolutionarily conserved. It has been shown that miRNAs regulate various physiological and pathological pathways such as cell differentiation, cell proliferation and tumorigenesis (reviewed in 4). Extensive studies to determine expression profile of miRNAs in human cancer has revealed cell-type specific miRNA fingerprint found in B cell chronic lymphocytic leukemia (B-CLL), breast cancer, colon cancer, gastric cancer, glioblastoma, hepatocellular carcinoma, papillary thyroid cancer, and endocrine pancreatic tumors (reviewed in 5).

Calin et al. showed that although miRNA genes represent only 1% of the mammalian genome, more than 50% of miRNA genes are located within region associated with amplification, deletion and translocation in cancer (6). Such somatic changes of miRNA genes definitively attribute to the specific expression pattern found in cancer. Additional factors, which attribute to the cancer specific deregulation of miRNAs, are unknown, although the most obvious candidate is transcriptional control. Other possibility is that miRNA maturation is such factor. Micro RNA biogenesis begins with a primary transcript, termed pri-miRNA, which is generated by RNA polymerase II (review in 7). Within the pri-miRNA, the miRNA itself is contained within a ~60-80 nucleotide that can fold back on itself to form a stem-loop hairpin structure. This hairpin structure is recognized and excised from pri-miRNA by the microprocessor complex composed of nuclear RNase III enzyme, Drosha and its binding partner DGCR8. The excised miRNA hairpin, referred to as pre-miRNA, is transported to the cytoplasm in association with RAN-GTP and Exportin 5, where it is further processed by a second RNase III enzyme, Dicer, which releases a 22 nucleotide mature duplex RNA with 5' phosphate and 2-nucleotide 3' overhang. The antisense RNA strand is incorporated into the RISC complex, which target it to mRNA(s) by base-pairing and consequently interfere with translation of the mRNA or cleave it. In principle, any step during this maturation process could affect miRNA production.

Consequently, there is a need for agents that regulate gene expression via the mechanisms mediated by small non-coding RNAs. Identification of oligomeric compounds that can increase or decrease gene expression or activity by modulating the levels of miRNA in a cell is therefore desirable.

The present invention therefore provides oligomeric compounds and methods useful for modulating the levels, expression, or processing of pri-miRNAs, including those relying on mechanisms of action such as RNA interference and dsRNA enzymes, as well as antisense and non-antisense mechanisms. One having skill in the art, once armed with this disclosure will be able, without undue experimentation, to identify compounds, compositions and methods for these uses.

SUMMARY OF THE INVENTION

The present invention is based on the discovery that All1 fusion protein-mediates the recruitment of the enzyme Drosha to target genes encoding specific miRNAs. This recruitment is now believed to be the cause for the enhanced expression of the relevant miRNAs.

In one aspect, there is provided agents that regulate gene expression via the mechanisms mediated by small non-coding RNAs. Identification of oligomeric compounds that can increase or decrease gene expression or activity by modulating the levels of miRNA in a cell is therefore desirable.

In a particular aspect, there is provided oligomeric compounds and methods useful for modulating the levels, expression, or processing of pri-miRNAs, including those relying on mechanisms of action such as RNA interference and dsRNA enzymes, as well as antisense and non-antisense mechanisms. One having skill in the art, once armed with this disclosure will be able, without undue experimentation, to identify compounds, compositions and methods for these uses.

In a particular aspect, there is provided oligomeric compounds, especially nucleic acid and nucleic acid-like oligomeric compounds, which are targeted to, or mimic, nucleic acids comprising or encoding small non-coding RNAs, and which act to modulate the levels of small non-coding RNAs, particularly pri-miRNAs, or interfere with their function.

In a particular aspect, there is provided oligomeric compounds, especially nucleic acid and nucleic acid-like oligomeric compounds, which are targeted to pri-miRNAs, and which act to modulate the levels of pri-miRNAs, or interfere with their processing or function.

In a particular aspect, there is provided oligomeric compounds that target a region flanking or overlapping a Drosha recognition region within a pri-miRNA.

Additionally, there is provided oligomeric compounds that target a region flanking or overlapping a Drosha cleavage site. There is also provided oligomeric compounds that increase levels of a pri-miRNA. For example, the present invention provides oligomeric compounds 15 to 30 nucleobases in length targeted to a Drosha recognition region within a polycistronic pri-miRNA transcript. The polycistronic pri-miRNA transcript can be that from which the miRNAs listed in Table 1 are derived.

In particular embodiments, the Drosha recognition region can be one or more of the miRNAs listed in Table 1. Such oligomeric compounds may be antisense oligonucleotides, and may contain one or more chemical modifications. Additionally, such oligomeric compounds are capable of increasing pri-miRNA levels.

Also provided are methods of modulating the levels of small non-coding RNAs, particularly pri-miRNAs, in cells, tissues or animals comprising contacting the cells, tissues or animals with one or more of the compounds or compositions of the invention.

Further provided are methods of modulating the levels of miRs derived from a polycistronic pri-miR transcript in a cell comprising selecting a polycistronic pri-miR transcript, selecting a Drosha recognition region of a single miRNA derived from the selected polycistronic pri-miR transcript, selecting an oligomeric compound 15 to 30 nucleotides in length targeted to or sufficiently complementary to the selected Drosha recognition region, and contacting the cell with the oligomeric compound.

Such methods include modulating the levels of a single mature miRNA derived from the selected polycistronic pri-miRNA, or alternatively modulating the levels of two or more mature miRNAs derived from the selected polycistronic pri-miRNA.

Also provided are methods of modulating the levels of pri-miRNAs from those listed in Table 1 comprising contacting a cell with an oligomeric compound targeted to or sufficiently complementary to Drosha-recognition regions on such pri-miRNAs.

There is also provided herein methods for selectively modulating a single member of a miR family in a cell comprising selecting a member of a miR family derived from a pri-miR transcript, identifying one or more oligomeric compounds targeted to or sufficiently complementary to the Drosha recognition region of a the selected pri-miR transcript, wherein the identified oligomeric compounds lack sufficient complementarity to the Drosha recognition regions of pri-miR transcripts from which other members of the miR family are derived, and contacting the cell with such an identified oligomeric compound.

There is also provided herein oligomeric compounds comprising a first strand and a second strand wherein at least one strand contains a modification and wherein a portion of one of the oligomeric compound strands is capable of hybridizing to a small non-coding RNA target nucleic acid.

There is also provided herein oligomeric compounds comprising a first region and a second region and optionally a third region wherein at least one region contains a modification and wherein a portion of the oligomeric compound is capable of hybridizing to a small non-coding RNA target nucleic acid.

There is also provided herein methods for identifying oligomeric compounds capable of modulating pri-miRNA levels. A pri-miRNA is selected, and oligomeric compounds are designed such that they are targeted to or sufficiently complementary to various target segments within a pri-miRNA sequence, including oligomeric compounds targeted to and overlapping the mature miRNA sequence within the pri-miRNA. An increase in the level of a pri-miRNA in cells contacted with the oligomeric compounds as compared to cells not contacted with the oligomeric compounds indicates that the oligomeric compound modulates the pri-miRNA level.

There is also provided herein methods for identifying small molecules capable of modulating pri-miRNA levels. A pri-miRNA is selected, and small molecules are evaluated for their ability of modulate pri-miRNA levels. The small molecules may bind to the regions of the pri-miR containing or overlapping the mature miRNA sequence, or the Drosha recognition region. An increase in the level of a pri-miRNA in cells contacted with the small molecules as compared to cells not contacted with the small molecules indicates that the small molecule modulates the pri-miRNA levels.

There is also provided herein a decoy for treating and/or preventing ALL and -related diseases.

These as well as other important aspects of the invention will become more apparent from the following detailed description.

BRIEF DESCRIPTION OF THE DRAWINGS

The patent or application file contains at least one drawing executed in color. Copies of this patent or patent application publication with color drawings will be provided by the Office upon request and payment of the necessary.

20 μg of total RNAs were hybridized overnight at 43° C. with in vitro transcribed anti-sense probe of miR-191 or miR-155 and subsequently treated with RNase. Protected probe fragments were resolved on a 15% polyacrylamide gel containing 8M urea. End-labeled φX174/Hinf I was used as a molecular weight marker. Because of the compression of the marker for sizes larger than 200 nucleotides, only fragments of 151 nt and below are shown. As a loading control, 10 μg of total RNA was also subjected to hybridization with Cyclophillin probe.

Figure 2A:
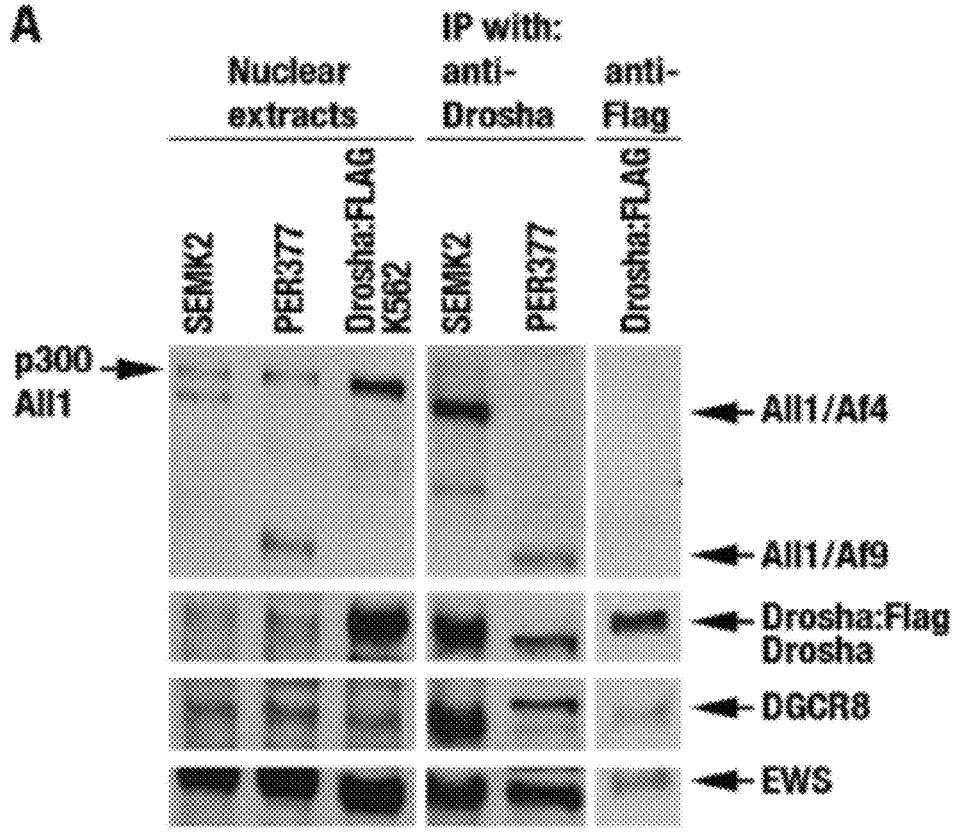
Figure 2B:
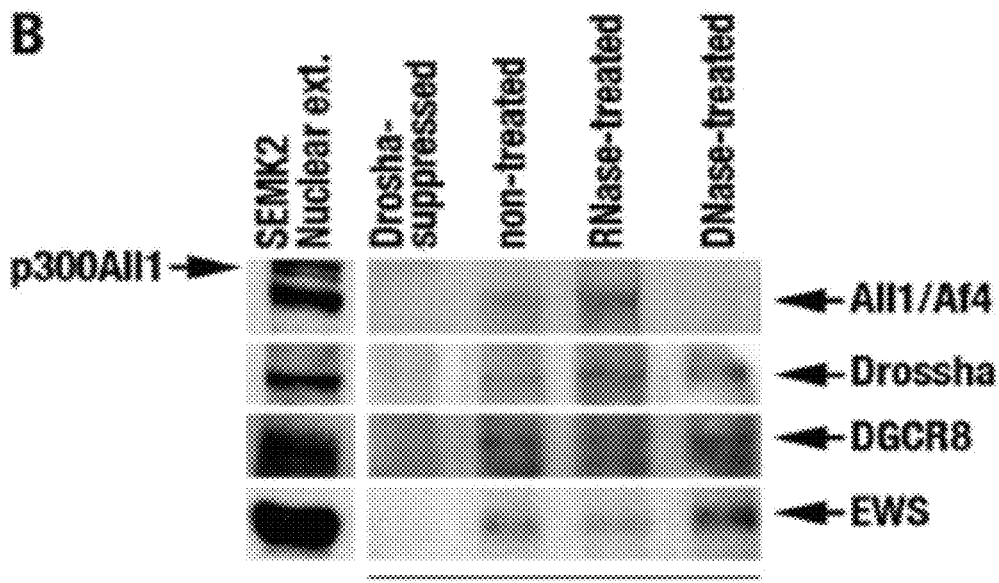

FIGS. 2A and 2B. Purification of Drosha protein from ALL-1-rearranged leukemic cells by Immunoprecipitation with anti-Drosha Ab.

FIG. 2A) Western blot detection of immunoprecipitated proteins. Ab 169 reacting with All1 N terminal epitope was utilized for the detection of All1/Af4 and of All1/Af9. For unambiguous identification of Drosha, recombinant Drosha exogenously expressed in K562 cells transfected with pCK-Drosha-Flag plasmid was purified by IP (Drosha:FLAG). 20 μg nuclear extracts of leukemic cells or around 2.5 μg of immuno-purified Drosha were used in the analysis. Note that endogenous Drosha was purified from nuclear extracts while Drosha:FLAG was from whole cell lyzate.

FIG. 2B) Western blot detection of proteins immunoprecipitated with anti-Drosha Ab from SEMK2 nuclear extracts treated either with RNase or DNase.

Figure 3:
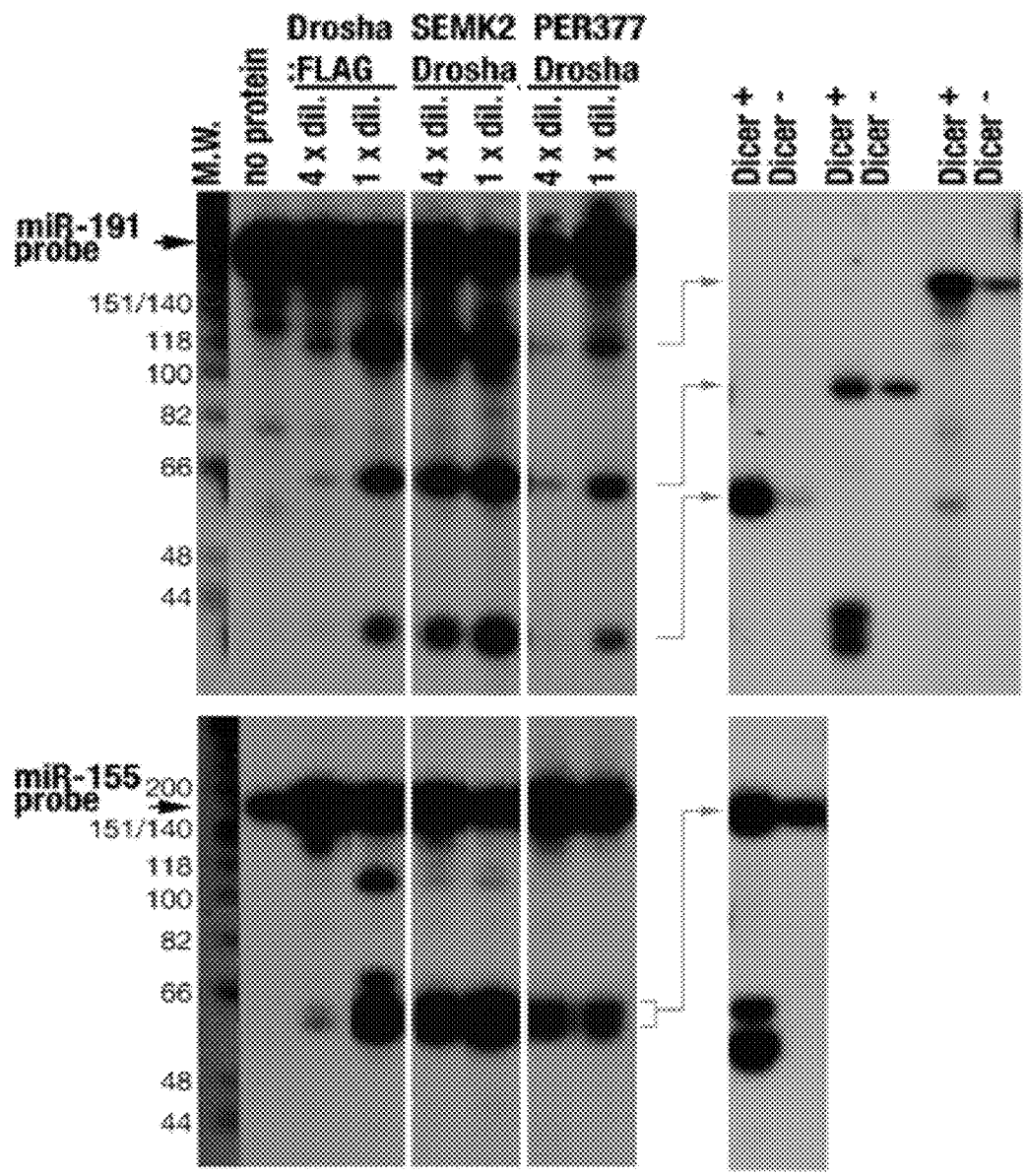

FIG. 3. In vitro cleavage assays of Drosha immuno-purified from plasmid-transfected cells and from ALL1-associated leukemic cell lines.

Equal amounts of Drosha, determined by Western analysis (FIG. 2A) were used in all reactions; the corresponding volumes of the non-diluted samples were 10 μl of Drosha:FLAG, 5 μl of SEMK2 Drosha and 20 μl of PER377 Drosha. Cleaved products of miR-191 and miR-155 were resolved on denaturing 9% polyacrylamide gel (FIG. 3, left). The cleaved products were excised from the gel, electro-eluted, and subjected to further cleavage with recombinant Dicer enzyme. 15% denaturing gel was used to resolve and identify the 22 nucleotides mature products (FIG. 3, right).

FIGS. 4A-E. All1/Af4-dependent localization of Drosha in miR-191 and miR-23a genomic loci and the effect of All1/Af4 knockdown on Drosha recruitment.

Figure 4A:
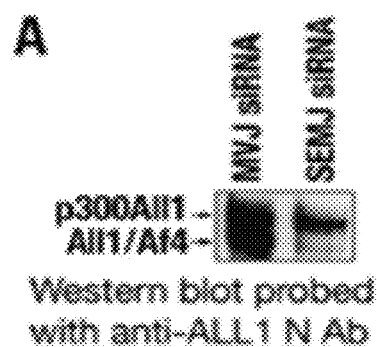

FIG. 4a) Elimination of most of the All1/Af4 protein from SEMK2 cells treated with SEMJ siRNA.

Figure 4B:
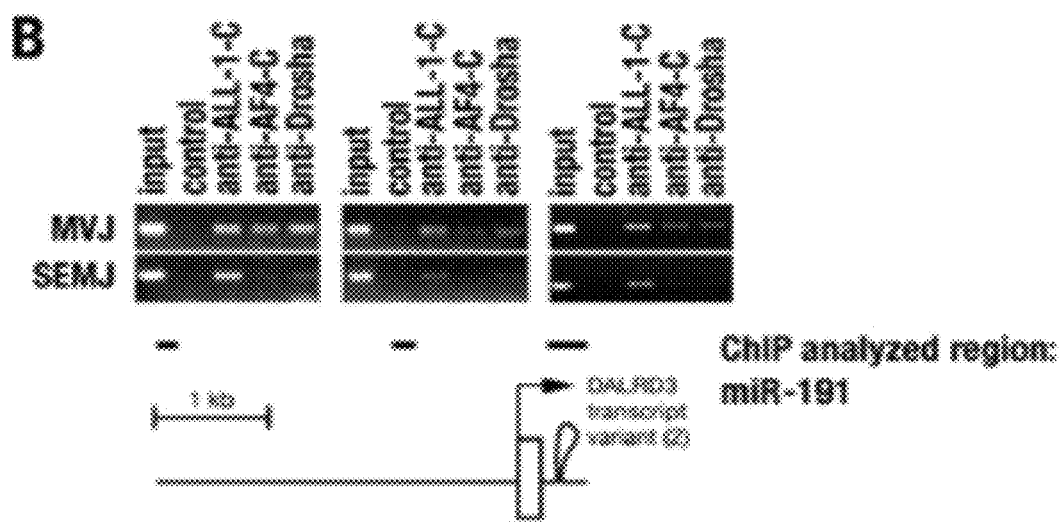
Figure 4C:
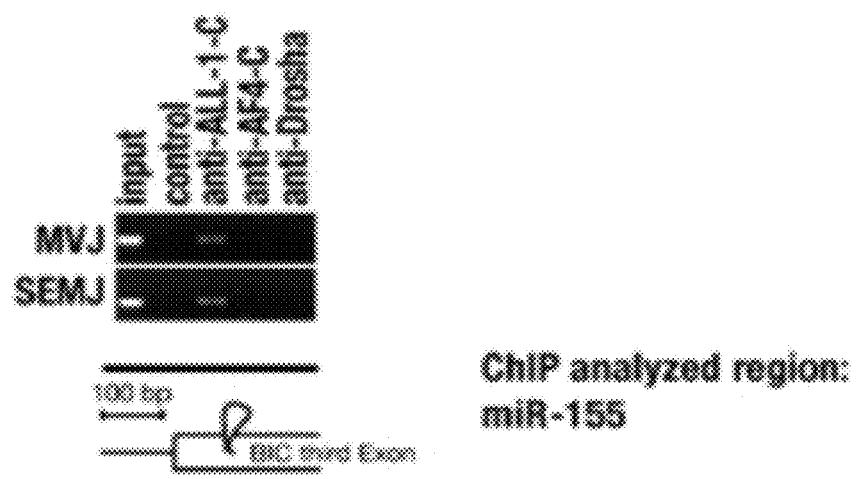
Figure 4D:
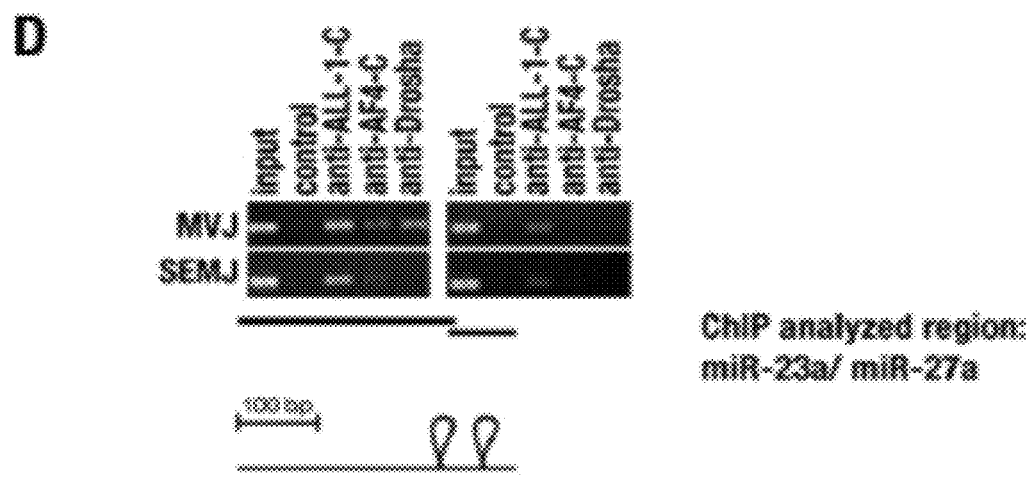

FIGS. 4B-4D) ChIP analysis for determination of recruitment of normal All1, All1/Af4 and drosha proteins to genomic loci encoding miR-191, miR-155, miR-23a and miR-27a. Chromatins tested were from SEMK2 cells treated with the non-functional siRNA MVJ, or from cells treated with the SEMJ siRNA which knocks down most of All1/Af4.

FIG. 4E) The sequence listings for Nucleotide Sequence of Human Genomic fragment encoding microRNA-191 [SEQ ID NO.: 17], which was cloned into pGEM3Z vector (Promega) and was used as a probe in RNase protection assay; Nucleotide Sequence of Human Genomic fragment encoding microRNA-155 [SEQ ID NO.: 18], which was cloned into pGEM3Z vector (Promega) and was used as a probe in RNase protection assay; Nucleotide Sequence of Human Genomic fragment encoding microRNA-23a [SEQ ID NO.: 19], which was cloned into pGEM3Z vector (Promega) and was used as a probe in RNase protection assay; Nucleotide Sequence of Human Genomic fragment encoding microRNA-27a [SEQ ID NO.: 20], which was cloned into pGEM3Z vector (Promega) and was used as a probe in RNase protection assay.

Figure 5:
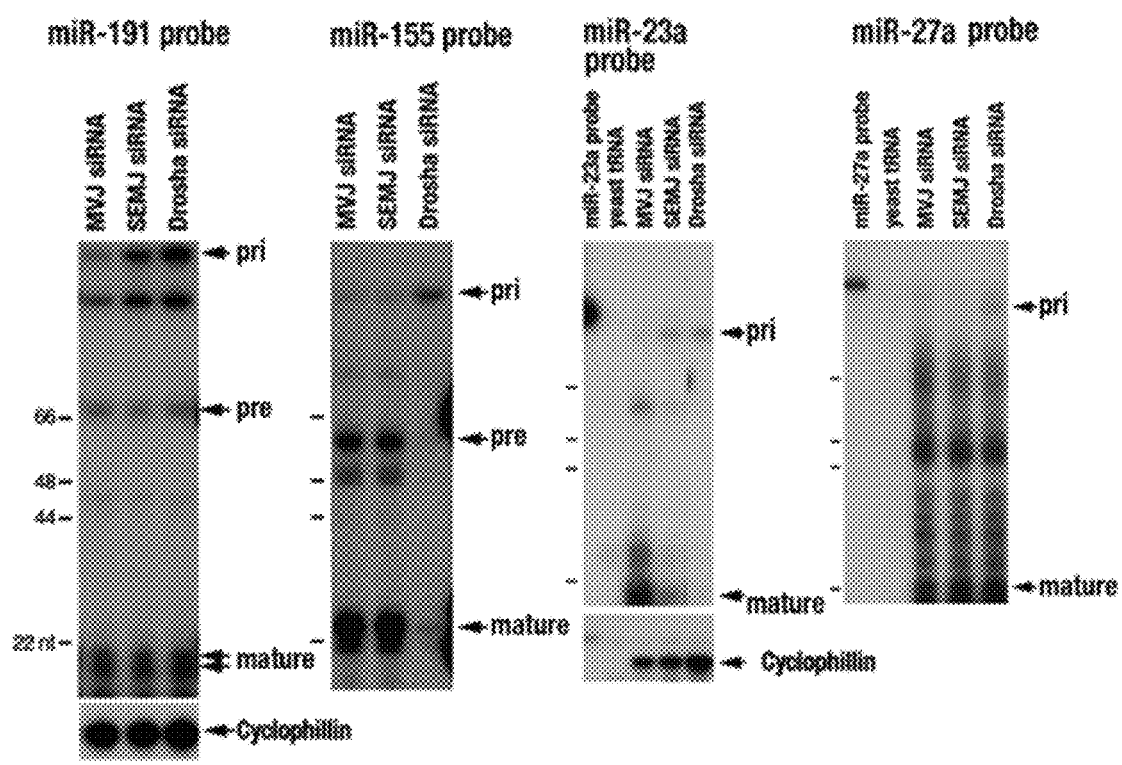

FIG. 5. Effect of All1/Af4 knockdown on accumulation of pri miR-191.

Abundance of the precursors pri miR-191, pri miR-155, pri miR-23a and pri miR-27a, as well as of their processed products, was tested in SEMK2 cells treated with the non-active MVJ siRNA, or knocked down for either All1/Af4 (SEMJ) or Drosha. The RNAs were identified by RNase protection assay (see text). Note that Drosha knockdown increased the abundance of all primary transcripts. In contrast, knockdown of All1/Af4 (SEMJ) was associated with higher abundance of pri miR-191 and pri miR-23a.

Figure 6:
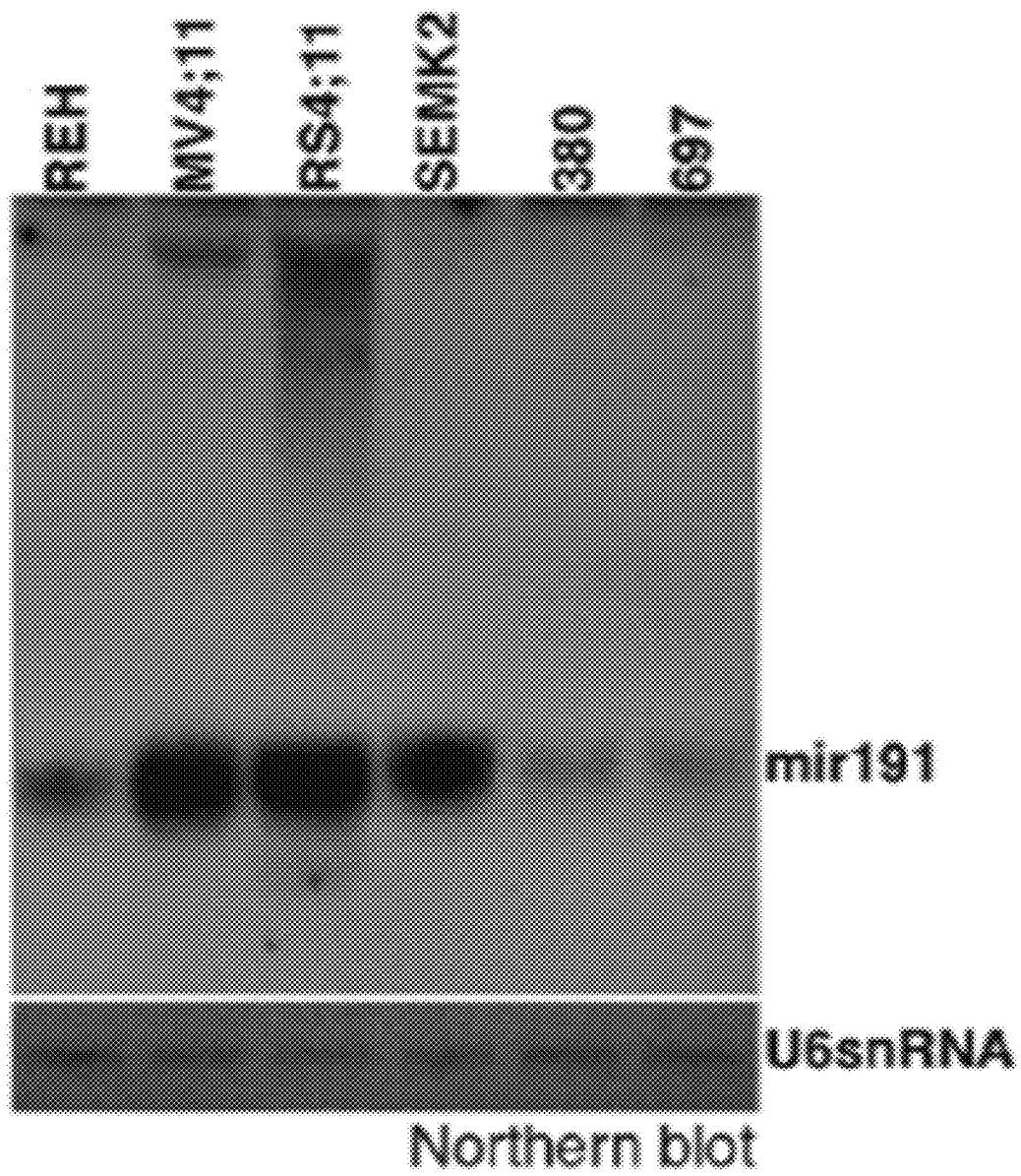

FIG. 6. Upregulation of miR-191 in leukemic cell lines with the t(4;11) chromosome translocation.

Northern analysis of RNAs (aliquots of 20 μg) from MV4;11, RS4;11, and SEMK2—all pro-B cells with t(4;11), from the pro-B cells REH and 380, and from the pre-B cell line 697. RNAs were separated on 20% denaturing polyacrylamide gel and electro-blotted into a Nylon membrane. The 22 nucleotides miR-191 was identified by hybridization to an end-labelled oligonucleotide. Similar Northern analysis for KG1 and K562 cells, both lacking ALL1 rearrangement, indicated low level of expression like that of 380 and 697 cells (not shown).

Figure 7A:
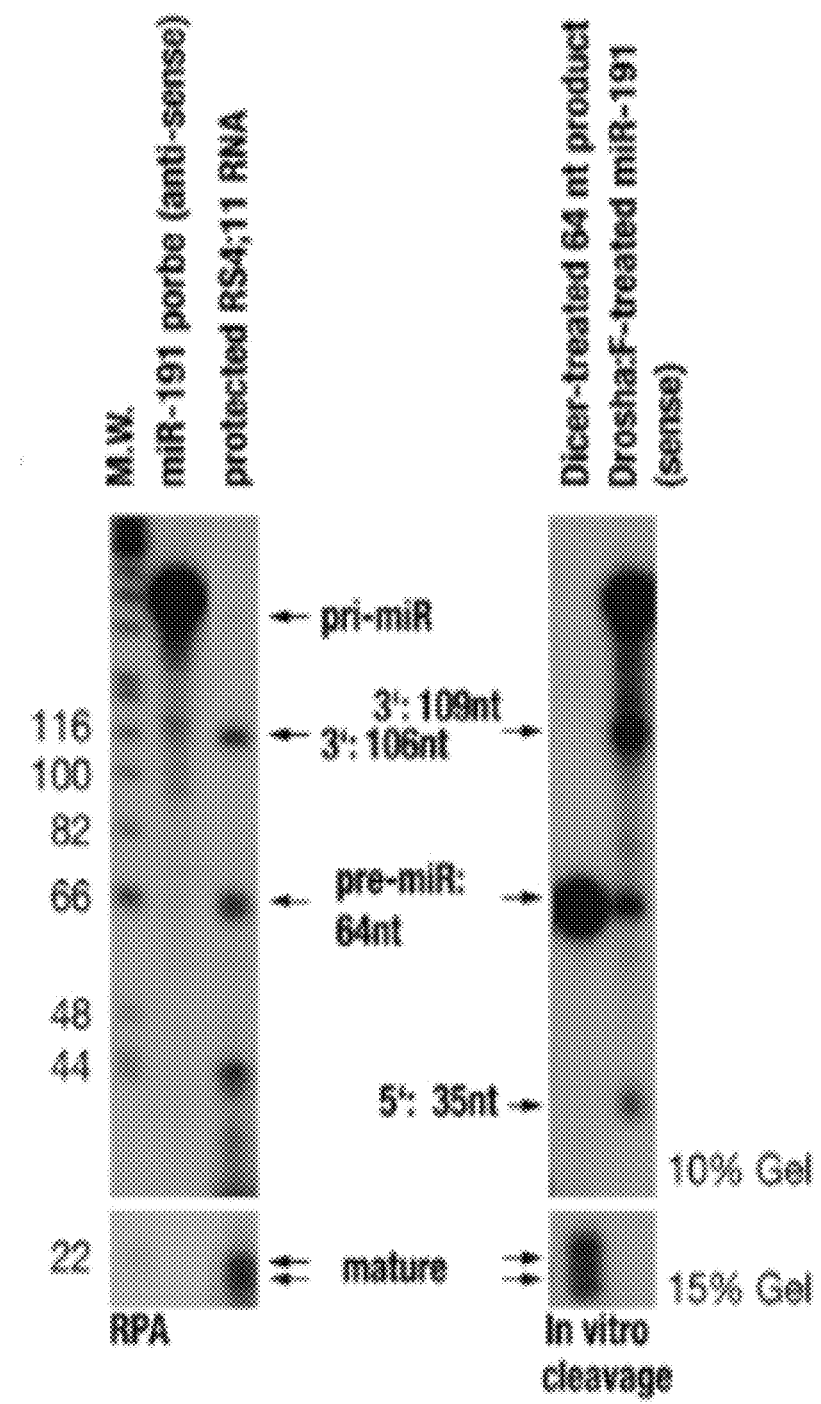
Figure 7B:
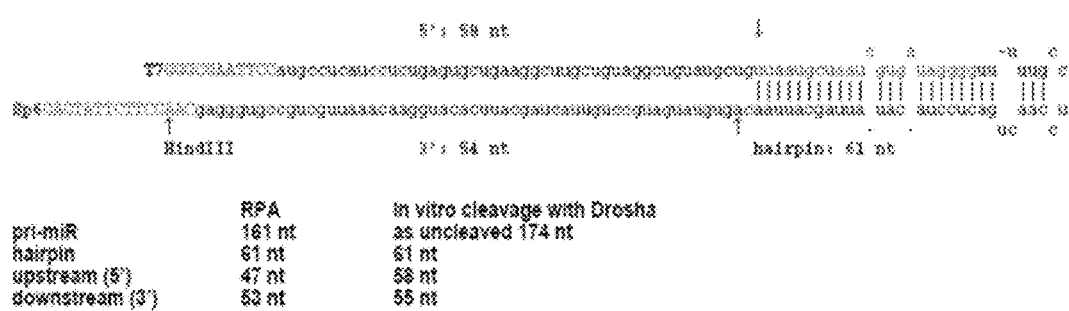

FIGS. 7A and 7B. Identification by RNase protection assay (RPA) of miR precursor and processed RNAs produced in vivo (left gels), or produced by in vitro cleavage with Drosha and Dicer (right gels).

Sequences of miR-191 [SEQ ID NO: 21] probe (FIG. 7A) and miR-155 probe [SEQ ID NO: 22] (FIG. 7B), synthesized by in vitro transcription with T7 RNA polymerase are shown. The mature micro RNA and the flanking pGEM 3Z vector sequences are shown in red and grey letters, respectively. Restriction sites used to generate run-off transcripts are indicated. Vertical arrows indicate Drosha cleavage sites, predicted from ref.11 for miR-191 or reported in ref. 9 for miR-155. Predicted RNase protected fragments of the products of hybridization between cell RNA and uniformly labeled probes, and of in vitro cleavage products (by Drosha or Dicer) are summarized below the probe sequence. Products of the RPA and of the in vitro cleavage assays were resolved on a single denaturing gel. For the in vitro cleavage assay, Drosha:FLAG was used. The cleavage products of 64 and 61 nt, derived from miR-191 and miR-155 probes, respectively, were digested with recombinant Dicer after excision and purification from the gel. In the assay for miR-155, the RPA protected fragments of 53 and 61 nt and the in vitro cleavage products could not be resolved in the gel and their relative positions are marked with arrows.

FIGS. 8A and 8B. miR-23a probe [SEQ ID NO: 23] (FIG. 8A) and miR-27a probe [SEQ ID NO: 24] (FIG. 8B) used in RNase Protection Assay in FIG. 5.

The mature micro RNA and the flanking pGEM 3Z vector sequences are shown in red and grey letters, respectively. The pGEM 3Z recombinants harboring miR-23a hairpin and miR-27a hairpin were linearlized with NaeI and Bsu36I, respectively and were used as the templates to generate anti-sense probes with SP6 RNA polymerase.

DETAILED DESCRIPTION OF THE INVENTION

A description of particular embodiments of the invention follows.

As used herein, the term "Drosha recognition region" within a pri-miRNA transcript encompasses the mature miRNA as well as up to 25 nucleotides in the 5' direction relative to the 5' Drosha cleavage site of such mature miRNA, and up to 50 nucleotides in the 3' direction relative to the 3' Drosha cleavage site of such mature miRNA. In additional embodiments, the Drosha recognition region encompasses the mature miRNA and up to 15 nucleotides in the 5' direction relative to the 5' Drosha cleavage site of such mature miRNA, and up to 40 nucleotides in the 3' direction relative to the 3' Drosha cleavage site of such mature miRNA. In some aspects, the Drosha recognition region is a region strongly affected by oligomeric compounds targeted to this region, i.e. the targeting of oligomeric compounds to this region of a pri-miRNA results in a greater than 3.5-fold increase in the level of the pri-miRNA. In other aspects, the level of the pri-miRNA is moderately affected by oligomeric compounds targeted to this region, i.e. the targeting of oligomeric compounds to this Drosha recognition region results in a 1.5 to 2.5-fold increase in the levels of the pri-miRNA.

As used herein, the term "Drosha cleavage site" is used to refer to a site approximately 22 nucleobases from the junction of the terminal hairpin loop and the stem of a pri-miRNA. One end of the miRNA is determined by selection of the cleavage site by the Drosha enzyme.

Identification of miRNAs Deregulated in Leukemic Cell Lines Harboring ALL1 Rearrangements.

Applying miRNA microarray analysis, we determined the miRNA expression profiles of human leukemic cell lines harboring ALL1 rearrangements. A total of 18 miRNAs were found to be upregulated at statistical significance in cell lines with rearranged ALL1, including SEMK2 and RS4;11 cells with the t (4;11) and PER377 cells with the t (9;11). Two pro-B cell lines with no ALL1 abnormalities, 380 and REH, did not show upregulation, as shown in Table 1.

Table 1 shows a comparison of micro RNA expression profiles of cells with and without ALL1 rearrangement. Micro RNA expression profiles were determined in triplicate by probing micro RNA-chip with total RNAs from three cell lines expressing ALL-1 fusion protein and two cell lines bearing similar phenotype but lacking ALL-1 abnormalities. Genomic loci of bold typed miRs have been previously identified as binding sites for normal ALL-1 (14).

TABLE 1

| SAM | FDR | |
|---|---|---|
| MicroRNA | Score* | (%)** |
| upregulated micro RNAs | | |
| hsa-mir-191 | 4.84 | 0 |
| hsa-mir-24-1 | 4.42 | 0 |

TABLE 1-continued

| SAM | FDR | |
|---|---|---|
| MicroRNA | Score* | (%)** |
| hsa-mir-221 | 4.27 | 0 |
| hsa-mir-24-2 | 3.91 | 0 |
| hsa-mir-192 | 3.84 | 0 |
| hsa-mir-222 | 3.75 | 0 |
| hsa-mir-196a-1 | 3.59 | 0 |
| hsa-mir-023b | 3.27 | 0 |
| hsa-mir-146a | 3.26 | 0 |
| hsa-mir-023a | 3.10 | 0 |
| hsa-mir-128b | 2.83 | 0 |
| hsa-mir-128a | 2.69 | 0 |
| hsa-mir-220 | 2.54 | 0 |
| hsa-mir-196b | 2.39 | 0 |
| hsa-mir-223 | 2.26 | 0 |
| hsa-mir-146b | 2.20 | 0 |
| hsa-mir-214 | 1.90 | 2.46 |
| hsa-mir-135a-1 | 1.90 | 2.46 |
| downregulated micro RNAs | | |
| hsa-mir-125b-1 | −3.86 | 0 |
| hsa-mir-125b-2 | −3.19 | 0 |
| hsa-mir-100 | −2.45 | 2.97 |

*SAM identifies genes with statistically significant scores (i.e. paired t tests). Each gene is assigned a score on the basis of its change in gene expression relative to the standard deviation of repeated measurements for that gene. Genes with scores greater than a threshold are deemed potentially significant.
**The percentage of such genes identified by chance is the q-value of False Discovery Rate. miR-155 and 27a, investigated in this paper, are not upregulated in the cell lines with ALL1 translocations.

Figure 1:
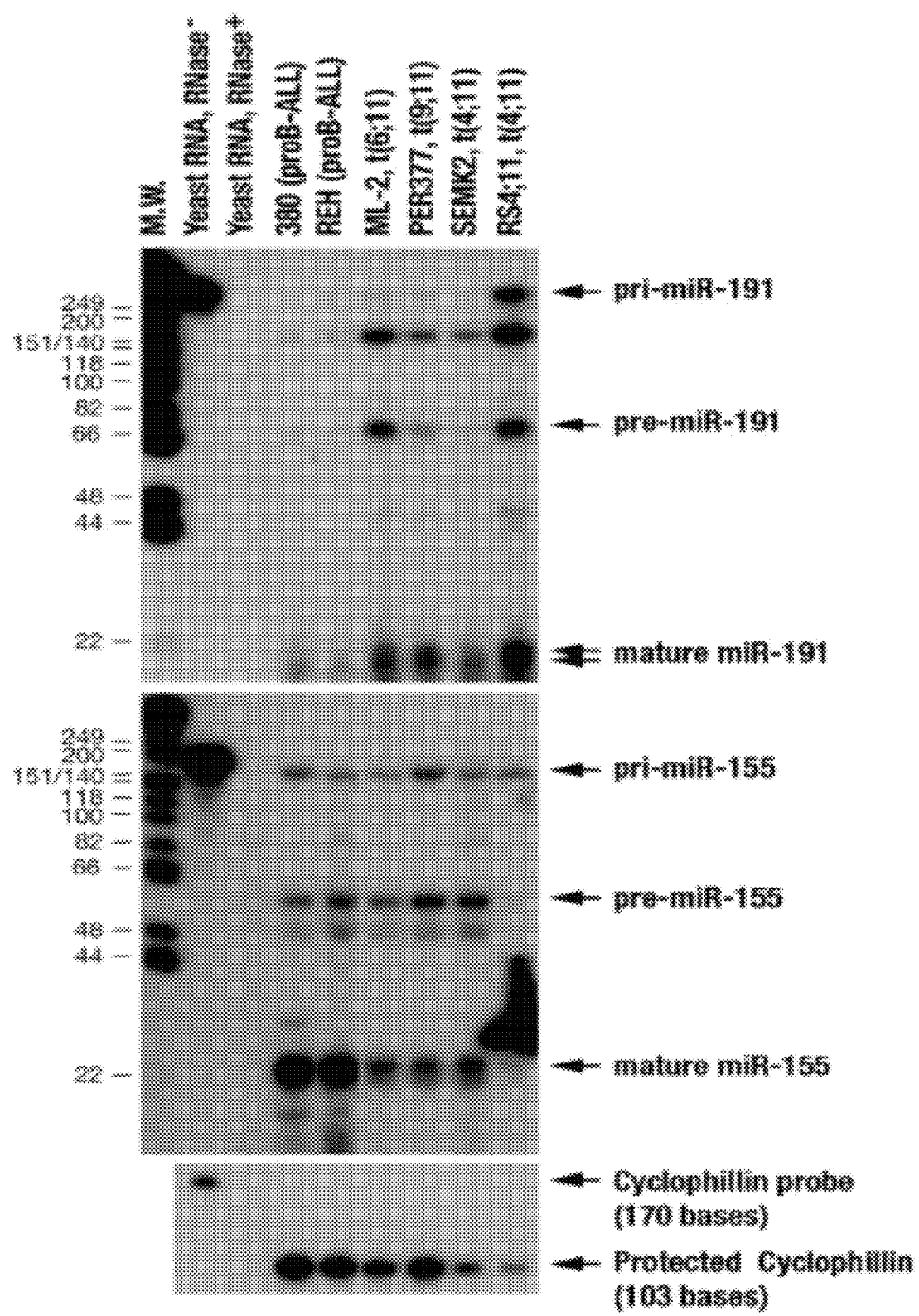
FIG. 1. RNase protection assay for the detection of miR-191 and miR-155 in leukemic cell lines with ALL-1 rearrangements.

Northern analysis supported and expanded these findings (see FIG. 6). To confirm and extend some of the results of the microarrays, the expression of miR-191, ranked top in the analysis, and miR-155 which did not show differential expression in lines with ALL1 gene rearrangements, were determined by applying RNase protection assay (see FIG. 1).

While miR-191 mature species could hardly be detected in REH and 380 cells, it was abundant in lines expressing All1 fusion proteins, including ML-2 with the t(6;11) chromosome translocation, PER377, SEMK2 and RS4;11 cells. In contrast, mature miR-155 was expressed in 380 and REH cells to considerably higher level compared to the other cells. This assay also showed that the degree of the pri-miR-191 protection (expression) was similar in all leukemic cells, except for RS4;11, regardless of the expression level of the mature species. This shows that the higher abundance of mature miR-191 in ALL1 associated leukemias is not due to overproduction of the pri-miRNA.

All1 Fusion Proteins, All1/Af4 and All1/Af9, Physically Interact with Drosha In Vivo.

The localization of both Drosha and All1 fusion proteins to the cell nuclei indicates that the latter affects Drosha-mediated miR-191 processing. To test the physical interaction between Drosha and All1 fusion proteins, we applied coimmunoprecipitation methodology. It has been previously reported that the exogenously expressed Drosha:FLAG assembles a complex, termed the microprocessor complex (8, 9, 10). In addition, Drosha:FLAG was found to assemble a second and larger multiprotein complex of >2 MDa which contained many RNA binding proteins including EWS (10). We used anti-Drosha Ab to precipitate endogenous Drosha produced in SEMK2 and PER377 cell nuclei.

In parallel, Drosha-Flag was precipitated with anti-Flag mAb from whole cell lysates of transfected K562 cells. Drosha in the immunoprecipitates were eluted by adding excess amount of the synthetic peptide previously used to generate the Ab. The eluates were subjected to Western blot analysis (see FIG. 2), as well as to in vitro cleavage assays to measure processing of miR-191 and miR-155 probes (see FIG. 3).

The Western blot analysis demonstrated co-immunoprecipitation of two known Drosha-associated proteins, DGCR8 and EWS (see FIG. 2A). Strikingly, the fusion proteins All1/Af4 and All1/Af9 co-precipitated with Drosha (ibid). In contrast, normal p300 All1 did not co-precipitate. Reciprocal immunoprecipitation directed against All1/Af4 by using anti-Af4C-terminal Ab failed to co-immunoprecipitate Drosha, although this Ab effectively precipitates the fusion protein (data not shown). The co-immunoprecipitaion of the All1 fusion proteins with Drosha is not due to cross-reaction, because the anti-Drosha Ab did not precipitate All1/Af4 from SEMK2 cells in which the Drosha protein was downregulated by interference RNA (see FIG. 2B).

The failure of anti-Af4 Ab to coprecipitate Drosha indicates that only a small portion of All1/Af4 is associated with Drosha or that the association masks the relevant epitope on Af4 C-terminal region. We next sought to determine whether the association between All1/Af4 and Drosha is RNA-dependent and/or DNA-dependent. To this end, SEMK2 nuclear extracts were treated extensively with either RNase or DNase and subjected to IP with anti-Drosha Ab. Western blot analysis showed the presence of All1/Af4, Drosha, DGCR8 and EWS proteins in the immunoprecipitate of RNase-treated nuclear extracts (FIG. 2B). Significantly, DNase treatment abrogated the association of Drosha with All1/Af4 while the association with other proteins was sustained (ibid). These results suggest that a genomic DNA is involved in the physical interaction between All1/Af4 and the Drosha complex.

The in vitro cleavage assays showed that all Drosha preparations generated three species of miR-191 cleavage products. Of these, the species of approx. 66 nucleotides was identified as pre-miR-191 because of its cleavage by recombinant Dicer enzyme (see FIG. 3, right). Similarly, the mixture of miR-155 processed products, surmised to be composed of three species of 55, 59 and 65 nucleotides was shown to be further cleaved by Dicer, resulting in generation of 22 bases products (ibid). These results indicated that the three affinity-purified Drosha preparations were functionally active with both miR-191 and miR-155 templates. Drosha containing All1/Af4 exhibited the strongest processing activity whereas Drosha containing All1/Af9 had less processing activity, similar to that of the Drosha:FLAG preparation.

All1/Af4-Mediated Drosha Recruitment to miRNA Loci.

The dependency of the physical interaction between All1/Af4 and Drosha on cellular DNA prompted us to investigate the occupancy of the two proteins on the miR-191 gene. We have also discovered that normal All1 binds to DNA regions located 3.5 and 1.5 kb upstream of miR-191 hairpin as well as to the region spanning the hairpin sequence itself (11). Chromatin immunoprecipitation analysis was done on: 1) SEMK2 cells transfected with SEMK2-fusion junction-specific siRNA; the latter downregulates the All1/Af4 protein at an efficiency of >90%, 2) SEMK2 cells expressing siRNA which targets a different ALL1/AF4 junction and therefore does not affect the level of the fusion protein in the cells (the two siRNAs are referred to as SEMJ and MVJ siRNA, respectively; the amount of All1/Af4 protein in the transfectants is shown in FIG. 4A).

The analysis of chromatin of cells containing MVJ siRNA, as well as of intact SEMK2 cells (not shown), showed co-occupancy of normal All1, All1/Af4 and Drosha proteins on the three regions within the miR-191 locus (see FIG. 4B). In contrast, no occupancy of All1/Af4 and Drosha on miR-155 hairpin was detected (see FIG. 4C).

Knockdown of All1/Af4 by treatment with SEMJ siRNA resulted in reduced occupancy of the fusion protein on the three sites within the miR-191 gene, and a concurrent loss of Drosha binding (see FIG. 4B). This indicates All1/Af4-mediated Drosha recruitment onto the miR-191 locus. The investigation was further extended to two additional micro RNA loci. The miR-23a and miR-27a genes are aligned in 5' to 3' configuration and are spaced by an interval of 84 nucleotides. The expression microarray analysis showed miR-23a, but not miR-27a, to be upregulated in leukemic cells expressing All1 fusion proteins (see Table 1).

The protein binding profiles of normal All1, All1/Af4 and Drosha within the miR-23a and 27a regions spanning the hairpin sequences resembled the profiles of miR-191 and miR-155, respectively (see FIG. 4D).

The binding of both All1/Af4 and Drosha to the miR-23a gene is reduced or eliminated (ibid) in SEMK2 cells knocked out for All1/Af4 (SEMJ).

All1/Af4 knockdown causes accumulation of specific pri-miRNAs.

To investigate the consequence of the reduction in amounts of All1/Af4 and Drosha bound to the genomic regions encoding miR-191 and miR-23a, we determined the expression level of primary and processed RNA products of the loci in comparison to those encoded by the miR-155 and miR-27a genes. The products from SEMK2 cells treated with MVJ siRNA, or SEMJ siRNA or Drosha-specific siRNA were analyzed by RNase protection assay (see FIG. 5).

Both All1/Af4 and Drosha knockdown resulted in accumulation of the primary transcript of miR-191 and miR-23a indicating impairment of Drosha function by either manipulation. The apparent impairment caused by both knockdown of Drosha and All1/Af4 is reflected in reduced abundance of the 22 bases mature miR-23a. In contrast, knockdown of All1/Af4 in cells treated with SEMJ siRNA did not increase the abundance of pri-miR-155 or pri-miR-27a compared to cells treated with the inert MVJ siRNA (knockdown of Drosha brought about accumulation of pri-miR-155 and pri-miR-27a). This indicates that elimination of All1/Af4 impairs processing of pri-miR-191 and pri-miR-23a, but not of pri-miR-155 or pri-miR-27a.

Discussion

Presented herein are several micro RNAs that have been identified as being upregulated in ALL1-associated leukemias. Further, we show that leukemogenic All1 fusion proteins, All1/Af4 and All1/Af9 physically interact with Drosha, the nuclear RNase III enzyme essential for micro RNA biogenesis. The notion that nuclear pri-miRNA processing mediated by Drosha and its associated protein(s) greatly affects miRNA production in vivo was first noticed in discrepancies between the levels of primary transcript, precursor, and mature miRNA species. Human embryonic stem cells express measurable amount of the primary transcript encoding let-7a-1 but lack mature species (12). Similarly, the level of miR-155 in diffuse large B cell lymphoma showed only a weak correlation with the level of BIC RNA in which miR-155 is contained (13).

Recent study to determine let-7g expression of all three molecular forms in mouse embryo showed that the mature species is detectable at 10.5 d gestation and is high at 14.5, whereas the primary transcript is highly expressed throughout development (14). Similar discrepancies were also found in several miRNAs known to be associated with mouse development. Since the accumulation of the precursor species was not detected, the differentiation events that occur during embryonic development activate Drosha processing of specific miRNA. In the same study, the authors further extended their findings to primary human tumors by comparing the data sets of primary transcripts and corresponding miRNA expressions and showed evidence supporting the Drosha processing block, which may cause the down-regulation of miRNAs observed in cancer (ibid). Apparently, exploration of molecular mechanisms underlying activation or inhibition of Drosha processing, directed against specific miRNA is the next need.

By applying ChIP analysis and RNase protection assay to leukemic cells expressing All1/Af4, or impaired in this expression due to enforced taking in of siRNA directed against the latter, the inventor herein now shows recruitment of both All1/Af4 and Drosha to a specific micro RNA genomic locus, and augmentation of processing of the primary transcript. The apparent enhanced production of the mature micro RNA in cell lines producing All1 fusion proteins is now believed to be due to Drosha binding to the corresponding locus.

In a particular aspect, there is provided herein a new mechanism by which micro RNAs may be regulated, and a new function for All1 leukemic proteins.

Upregulation of miR-191 is found to be associated with poor prognosis in acute myeloid leukemias (15). Upregulation of miR-191 is also observed in study of 6 different types of solid tumors including colon, breast and lung cancer (16)

EXAMPLES

Materials and Methods

Cell Culture and Antibodies.

Human pro-B ALL 380, pre-B ALL 697, ML-2 with the t(6;11), and SEMK2 and MV4;11 with the t(4;11) were obtained from DSMZ. REH pro-B ALL, RS4;11 with the t(4;11) and K562 were purchased from ATCC. PER377 with the t(9;11) was obtained from Dr. Ursulla Kees. All cell lines were maintained in RPMI 1640 medium supplemented with 10% fetal bovine serum. Antibodies against Drosha (ab12286), DGCR8 (ab24162) and a Drosha synthetic peptide (ab12307) were purchased from Abcam. Ab against EWS was made by Bethyl Laboratories (A300-308A). Anti-FLAG M2 mAb and 3xFLAG peptide were obtained from Sigma. Ab 169 directed against ALL-1 N-terminus was described (17). Ab against AF4 C-terminus was generated in rabbit by using bacterially synthesized polypeptide spanning AF4 residues 2323-2886.

Microarray Analysis.

Microarray analysis was performed as previously described (18). Raw data were normalized and analyzed in GENESPRING 7.2 software (zcomSilicon Genetics, Redwood City, Calif.). Expression data were median-centered by using both the GENESPRING normalization option and the global median normalization of the BIOCONDUCTOR package (www.bioconductor.org) with similar results. Statistical comparisons were done by using the GENESPRING ANOVA tool and the significance analysis of microarray (SAM) software.

miRNA Detection.

Figure 7B:
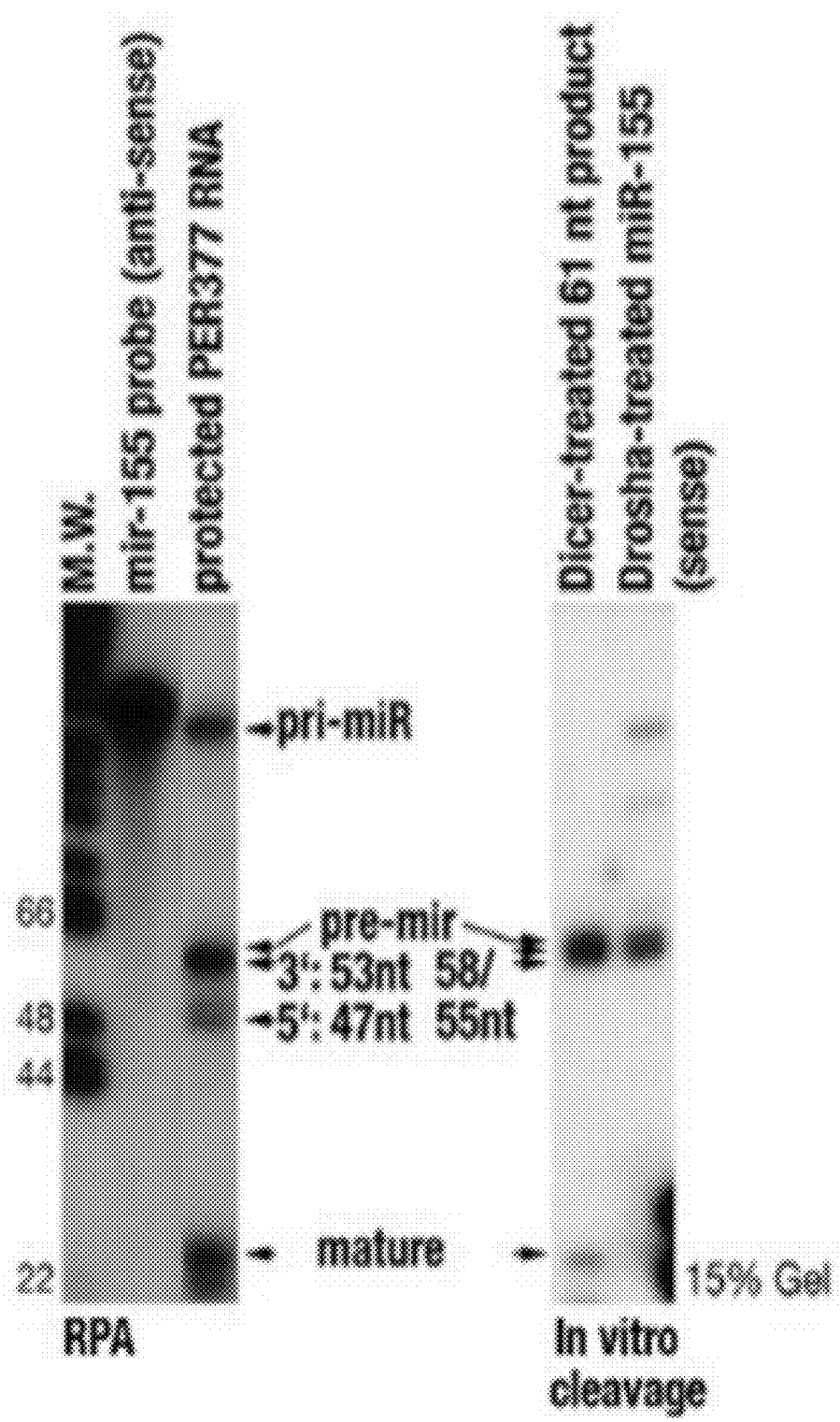

RNase Protection assays (RPA) were performed using RPA III kit from Ambion, according to the manufacturer's instructions. 5-20 µg of total RNA extracted with TRIZOL reagent (Invitrogen) were used per reaction. Cyclophillin antisense control template was obtained from Ambion and was labeled by utilizing T7 RNA polymerase. For the identification of protected species corresponding to pri-, pre- and mature miR-191 and miR-155, see FIG. 7.

Vector Construction and Probe Preparation.

A genomic fragment spanning miR-191 hairpin was prepared by digesting BAC clone RP13-131K19 with PflMI-Bsu36I, blunt-ending and subcloning into the SmaI site of pGEM-3Z (Promega) in both orientations. These constructs were linearlized with BamHI and used as templates for generating RNA probes by using Riboprobe in vitro transcription kit with T7 RNA polymerase (Promega). Probes with sense and anti-sense orientation were purified on a denaturing gel, and used in in vitro cleavage assay and in RNase protection assay, respectively. miR-155 hairpin region, embedded within the third exon of the BIC gene, was PCR-amplified from the human IMAGE cDNA clone 5176657.

The forward primer ATGCCTCATCCTCTGAGTGCT [SEQ ID NO: 1] tethered with EcoRI site and the reverse primer CTCCCACGGCAGCAATTTGTT [SEQ ID NO: 2] tethered with HindIII site, corresponding to nucleotides 261-281 and 401-421 (ref.13), respectively, were used for amplification.

Subsequently, the PCR product was cloned into the EcoRI-HindIII sites of the pGEM-3Z vector. Sense and anti-sense RNA probes were synthesized by using T7 RNA polymerase and SP6 RNA polymerase, respectively. Genomic regions spanning miR-23a and miR-27a hairpin sequences were PCR-amplified as shown in FIG. 8 and cloned into the HindIII-EcoRI sites of the pGEM3Z vector.

Anti-*SAM identifies genes with statistically significant scores (i.e. paired t tests). Each gene is assigned a score on the basis of its change in gene expression relative to the standard deviation of repeated measurements for that gene. Genes with scores greater than a threshold are deemed potentially significant.

**The percentage of such genes identified by chance is the q-value of False Discovery Rate. miR-155 and 27a, investigated in this paper, are not upregulated in the cell lines with ALL1 translocations.

Probes of miR-23a and miR-27a were prepared by digesting the recombinants with NaeI and Bsu36I, respectively, followed by in vitro transcription with Sp6 RNA polymerase.

Immunoprecipitation.

K562 cells were transfected with pCK-drosha-flag by using a Nucleofector apparatus according to the manufacturer's instructions (AMAXA). $2 \times 10^8$ transfected cells were lysed and subjected to IP with anti-Flag M2 mAb as described in ref.11. Briefly, 25 mg whole cell lysate were incubated with 500 µg mAb after preclearing with protein G Sepharose (GE Healthcare) at 4° C., 0/N. Immunocomplex was precipitated with protein G Sepharose, washed, and the Drosha:FLAG in the precipitate was eluted by adding 3xFLAG peptide at a concentration of 0.4 mg/ml in a buffer containing 30 mM Hepes, pH7.4/100 mM KCl/5% Glycerol/0.2 mM EDTA/7.5 mM $MgCl_2$/2 mM DTT. Elution was repeated three times, each for 30 min at RT, and eluates were combined. For immunoprecipitation of endogenous Drosha, 50 mg of nuclear extracts from SEMK2 or PER377 cells prepared by the method of Dignam et al. (19) were subjected to IP with 300 µg of anti-Drosha Ab. The anti-Drosha Ab, purchased from Abcam, was generated in rabbit by immunizing with a synthetic peptide derived from the N-terminal region of Drosha, and the peptide is commercially available.

The examples with small scale IP showed that the addition of excess Drosha peptide to anti-Drosha-immunoprecipitate releases Drosha; this procedure enabled purification of the Drosha complex in a native form. The peptide was used for the elution of Drosha at a concentration of 0.4 mg/ml. In some IPs, as shown in FIG. 2B, 250 µg of SEMK2 nuclear extracts were mixed either with 50 µL of DNase-free RNase (Roche) or with 50 U of RQ1 DNase (Promega) and subjected to preclearing with protein A Sepharose (GE Healthcare) at RT for 60 min. This was followed by IP with 10 µg of anti-Drosha Ab.

In Vitro Processing of pri-miRNAs.

In vitro processing assay was done essentially as described (8). Amounts to be added of Drosha:FLAG and of two Drosha preparations were determined by measuring the content of Drosha by Western blot analysis. Briefly, 20 µL of reaction mixtures containing immuno-purified Drosha, 7.5 mM $MgCl_2$, 20 U of RNase inhibitor (RNasin, Promega), 2 mM ATP, 2 mM DTT and $1 \times 10^5$ cpm of the labeled probe were incubated at 37° C. for 90 min. The reactions were terminated by adding 20 µL of buffer containing 20 mM Tris, pH8.0/10 mM EDTA/1% SDS/2 µg of proteinase K (Roche), followed by incubation at 45° C. for 30 min. After extraction with phenol/chloroform and chloroform, the processed products were ethanol-precipitated and resolved on a polyacrylamide gel containing 8M urea.

RNA Interference siRNA duplexes targeting ALL-1/AF4 and Drosha mRNAs in SEMK2 cells were transfected by applying the Amaxa Nucleofector using kit V and program T-20. 24 h after transfection, cells were harvested and subjected to a second transfection, and subsequently were grown in culture for additional 48 h. Target sequences of SEMJ siRNA and MVJ siRNA were 5'-AAGAAAAGCAGACCUACUCCA-3' [SEQ ID NO: 3], and 5'-AAGAAAAGGAAAUGACCCATT-3' [SEQ ID NO: 4], respectively.

The former si RNA targets ALL-1/AF4 mRNA produced in SEMK2 cells, while the latter targets ALL-1/AF4 mRNA produced in MV4;11 cells. Note that the first 8 nucleotides in both siRNAs correspond to ALL-1 mRNA sequence immediately 5' of the fusion point and are identical whereas the following 13 nucleotides correspond to AF4 sequences which vary between the fusions and accordingly between the siRNAs; thus, MVJ siRNA will be inactive in SEMK2 cells. The sequence of Drosha siRNA is from ref.10. The siRNAs were synthesized by Dharmacon.

Chromatin Immunoprecipitation (ChIP) Assay.

ChIP assays were performed using the ChIP assay kit from Upstate with minor modifications. Briefly, $5 \times 10^7$ formaldehyde-treated SEMK2 cells were lysed in 1 mL buffer containing 50 mM Hepes, pH7.4/140 mM NaCl/1% Triton X/0.1% Na-Deoxycholate/1× Complete protease inhibitor (Roche). 50 µL aliquot of the preparation was treated to reverse the cross-linking, deproteinized with proteinase K, extracted with phenol chloroform and determined for DNA concentration. An aliquot of chromatin preparation containing 25 µg DNA was used per ChIP. DNase free RNase (Roche) was added at a concentration of 200 µg/mL during reverse cross linking After deproteinization with proteinase K, DNA was purified in 50 µL TE by using PCR-purification kit (QIAGEN) according to the manufacturer's instructions. 1 µL aliquot was used for PCR. Primer sequences are listed in Table 2.

TABLE 2

Sequences of primers used in ChIP analysis in FIG. 4 (shown 5' to 3')

| ChIP analyzed region | Forward primer | Reverse primer |
| --- | --- | --- |
| 3.5 kb upstream of miR-191 hairpin | GTAGCTGCCACTACCACAGAT [SEQ ID NO: 5] | AGCCAGAGTCAGATGCTCAGT [SEQ ID NO: 6] |
| 1.5 kb upstream of miR-191 hairpin | TACAAGCTACGTAGCGCGAGA [SEQ ID NO: 7] | ACTCGGCCTCCTAAGACTGAGG [SEQ ID NO: 8] |
| miR-191 hairpin | GTTCCCTCTAGACTC CGTTTCA [SEQ ID NO: 9] | AGTCACTACCATTGC AGCCCTA [SEQ ID NO: 10] |
| miR-155 hairpin | TGAGCTCCTTCCTTTCAACAG [SEQ ID NO: 11] | GTTGAACATCCCAGTGACCAG [SEQ ID NO: 12] |
| miR-23a hairpin | TCTAGGTATCTCTGCCTCTCCA [SEQ ID NO: 13] | AGCATCCTCGGTGGCAGAGCTCA [SEQ ID NO: 14] |
| miR-27a hairpin | TGAGCTCTGCCACCGAGGATGCT [SEQ ID NO: 15] | ACAGGCGGCAAGGCCAGAGGA [SEQ ID NO: 16] |

Diagnostics, Drug Discovery and Therapeutics

The oligomeric compounds and compositions of the present invention can additionally be utilized for research, drug discovery, kits and diagnostics, and therapeutics.

For use in research, oligomeric compounds of the present invention are used to interfere with the normal function of the nucleic acid molecules to which they are targeted. Expression patterns within cells or tissues treated with one or more oligomeric compounds or compositions of the invention are compared to control cells or tissues not treated with the compounds or compositions and the patterns produced are analyzed for differential levels of nucleic acid expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

For use in drug discovery, oligomeric compounds of the present invention are used to elucidate relationships that exist between small non-coding RNAs, genes or proteins and a disease state, phenotype, or condition. These methods include detecting or modulating a target comprising contacting a sample, tissue, cell, or organism with the oligomeric compounds and compositions of the present invention, measuring the levels of the target and/or the levels of downstream gene products including mRNA or proteins encoded thereby, a related phenotypic or chemical endpoint at some time after treatment, and optionally comparing the measured value to an untreated sample, a positive control or a negative control. These methods can also be performed in parallel or in combination with other experiments to determine the function of unknown genes for the process of target validation or to determine the validity of a particular gene product as a target for treatment or prevention of a disease.

For use in kits and diagnostics, the oligomeric compounds and compositions of the present invention, either alone or in combination with other compounds or therapeutics, can be used as tools in differential and/or combinatorial analyses to elucidate expression patterns of a portion or the entire complement of non-coding or coding nucleic acids expressed within cells and tissues.

The specificity and sensitivity of compounds and compositions can also be harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that oligomeric compounds can be useful therapeutic modalities that can be configured to be useful in treatment regimes for the treatment of cells, tissues and animals, especially humans.

For therapeutics, an animal, preferably a human, suspected of having a disease or disorder presenting conditions that can be treated, ameliorated, or improved by modulating the expression of a selected small non-coding target nucleic acid is treated by administering the compounds and compositions. For example, in one non-limiting embodiment, the methods comprise the step of administering to or contacting the animal, an effective amount of a modulator or mimic to treat, ameliorate or improve the conditions associated with the disease or disorder. The compounds effectively modulate the activity or function of the small non-coding RNA target or inhibit the expression or levels of the small non-coding RNA target. In certain embodiments, the small non-coding RNA target is a polycistronic pri-miRNA, a monocistronic pri-miRNA, a pre-miRNA, or a miRNA. In additional embodiments, the small non-coding RNA target is a single member of a miRNA family. Alternatively, two or more members of an miRNA family are selected for modulation. In a further embodiment, the small non-coding RNA target is a selectively processed miRNA. In one embodiment, the level, activity or expression of the target in an animal is inhibited by about 10%. In another embodiment the level, activity or expression of a target in an animal is inhibited by about 30%. Further, the level, activity or expression of a target in an animal is inhibited by 50% or more, by 60% or more, by 70% or more, by 80% or more, by 90% or more, or by 95% or more.

In another embodiment, the present invention provides for the use of a compound of the invention in the manufacture of a medicament for the treatment of any and all conditions associated with miRNAs and miRNA families.

The reduction of target levels may be measured in serum, adipose tissue, liver or any other body fluid, tissue or organ of the animal known to contain the small non-coding RNA or its precursor. Further, the cells contained within the fluids, tissues or organs being analyzed contain a nucleic acid molecule of a downstream target regulated or modulated by the small non-coding RNA target itself.

Compositions and Methods for Formulating Pharmaceutical Compositions

In another aspect, there is provided herein pharmaceutical compositions and formulations that include the oligomeric compounds, small non-coding RNAs and compositions of the invention. Compositions and methods for the formulation of pharmaceutical compositions are dependent upon a number of criteria, including, but not limited to, route of administration, extent of disease, or dose to be administered. Such considerations are well understood by those skilled in the art.

The oligomeric compounds and compositions of the invention can be utilized in pharmaceutical compositions by adding an effective amount of the compound or composition to a suitable pharmaceutically acceptable diluent or carrier. Use of the oligomeric compounds and methods of the invention may also be useful prophylactically.

The oligomeric compounds and compositions encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the oligomeric compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions.

The term "pharmaceutically acceptable salts" refers to physiologically and pharmaceutically acceptable salts of the compounds and compositions of the invention: i.e., salts that retain the desired biological activity of the parent compound and do not impart undesired toxicological effects thereto. Suitable examples include, but are not limited to, sodium and potassium salts.

In some embodiments, an oligomeric compound can be administered to a subject via an oral route of administration. The subject may be a mammal, such as a mouse, a rat, a dog, a guinea pig, or a non-human primate. In some embodiments, the subject may be a human or a human patient. In certain embodiments, the subject may be in need of modulation of the level or expression of one or more pri-miRNAs as discussed in more detail herein. In some embodiments, compositions for administration to a subject will comprise modified oligonucleotides having one or more modifications, as described herein.

Cell Culture and Oligonucleotide Treatment

The effects of oligomeric compounds on target nucleic acid expression or function can be tested in any of a variety of cell types provided that the target nucleic acid is present at measurable levels. This can be readily determined by methods routine in the art, for example Northern blot analysis, ribonuclease protection assays, or real-time PCR. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.

Any of the methods for gene therapy available in the art can be used according to the present invention. For general reviews of the methods of gene therapy, see Goldspiel et al., 1993, Clinical Pharmacy 12:488 505; Wu and Wu, 1991, Biotherapy 3:87 95; Tolstoshev, 1993, Ann. Rev. Pharmacol. Toxicol. 32:573 596; Mulligan, 1993, Science 260:926 932; and Morgan and Anderson, 1993, Ann. Rev. Biochem. 62:191 217; May, 1993, TIBTECH 11(5):155 215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

REFERENCES

The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims. Citation of a reference herein shall not be construed as an admission that such reference is prior art to the present invention.

1. Gu, Y., Nakamura, T., Alder, H., Prasad, R., Canaani, O., Cimino, G., Croce, C. M. & Canaani, E. (1992) *Cell* 71, 701-709.
2. Tkachuk, D. C., Kohler, S. & Cleary, M. L. (1992) *Cell* 71, 691-700.
3. Johansson, B., Moorman, A. V., Haas, O. A., Watmore, A. E., Cheung, K. L., Swanton, S. & Secker-Walker, L. M. (1998) *Leukemia* 12, 779-787.
4. Bartel, D. P. (2004) *Cell* 116, 281-297.
5. Calin, G. A. & Croce, C. M. (2006) *Nature Rev. Cancer* 6, 857-866 (2006).
6. Calin, G. A., Sevignani, C., Dumitru, C. D., Hyslop, T., Noch, E., Yendamur, S., Shimizu, M., Rattan, S., Bulrich, F., Negrini, M., et al. (2004) *Proc Natl Acad Sci USA*. 101, 2999-3004.
7. Kim, V. N. (2005) *Nature Rev. Mol. Cell Biol.* 6, 376-385.
8. Han, J., Lee, Y., Yeom, K. H., Kim, Y. K., Jin, H. & Kim, V. N. (2004) *Genes Dev.* 18, 3016-3027.
9. Landthaler, M., Yalcin, A. & Tuschl, T. (2004) *Current Biology* 14, 2162-2167.
10. Gregory, R. L., Yan, K-P., Amuthan, G., Chendrimada, T., Doratotaji, B., Cooch, N. & Shiekhattar, R. (2004) *Nature* 432, 235-240.
11. Guenther, M. G., Jenner, R. G., Chevailer, B., Nakamura, T., Croce, C. M., Canaani, E. & Young, R. A. (2005) *Proc. Natl. Acad. Sci. USA.* 102, 8603-8608.
12. Suh, M. R., Lee, Y., Kim, J. Y., Kim, S. K., Moon, S. H., Lee, J. Y., Cha, K. Y., Chung, H. M., Yoon, H. S., Moon, S. Y., et al. (2004) *Dev. Biol.* 270, 488-498.
13. Eis, P. S., Tam, W., Sun, L., Chadburn, A., Li, Z., Gomez, M. F., Lund, E. & Dahlberg, J. E. (2005) *Proc Natl Acad Sci USA.* 102, 3627-3632.
14. Thomson, J. M., Newman, M., Parker, J. S., Morin-Kensicki, E. M., Wright, T. & Hammond, S. M. (2006) *Genes Dev.* 20, 2202-2207.
15. Garzon, R. et al. MicroRNA signatures associated with cytogenetics and prognosis in acute myeloid leukemia. Submitted for publication.
16. Volinia, S., Calin, G. A., Liu, C-G., Ambs, S., Cimmino, A., Petrocca, F., Visone, R., Iorio, M., Roldo, C., Ferracin, M., et al. *Proc Natl Acad Sci USA.* 103, 2257-2261 (2006).
17. Nakamura, T., Mori, T., Tada, S., Krajewski, W., Rozovskaia, T., Wassell, R., Dubois, G., Mazo, A., Croce, C. M. & Canaani. E. (2002) *Mol Cell* 10, 1119-1128.
18. Liu, C.-G., Calin, G. A., Meloon, B., Gamliel, N., Sevignani, C., Ferracin, M., Dumitru, D. C., Shimizu, M., Zupo, S. & Dono, M., et al. (2004) *Proc. Natl. Acad. Sci. USA* 101, 9740-9744.
19. Dignam, J. D., Lebovitz, R. M. & Roeder, R. G. (1983) *Nucleic Acids Res.* 11, 1475-1489.

What is claimed is:

1. A method of determining whether a subject has, or is at risk for developing, acute lymphomic leukemia (ALL), wherein the method comprises:
   extracting from the subject a test sample, wherein the test sample comprises: at least miR-221 gene product; and blood, tissue and/or bone marrow having, or suspected of having, leukemic cells and/or leukemic lymphoblasts;
   measuring the level of the at least miR-221 gene product in the test sample;
   determining whether the subject has, or is at risk for developing, ALL by comparing the level of the at least miR-221 gene product in the test sample to the level of a corresponding miR gene product in a control sample,
   correlating an increase in the level of the at least miR-221 gene product in the test sample, relative to the level of the corresponding miR gene product in the control sample, as being indicative of a diagnosis of the subject either having, or being at risk for developing, ALL.

2. The method according to claim 1, wherein the measuring the level of the at least miR-221 gene product in the test sample is carried out by analyzing the test sample with a microarray and/or a Northern blot electrophoretic device.

3. A method of determining the prognosis of a subject having acute lymphomic leukemia (ALL) cancer, wherein the method comprises:
   extracting from the subject a test sample comprising at least miR-221 gene product;
   measuring the level of the at least miR-221 gene product in the test sample;
   determining the prognosis of the subject by comparing the level of the at least miR-221 gene product in the test sample to the level of a corresponding miR gene product in a control sample,
   correlating an increase in the level of the at least miR-221 gene product in the test sample, relative to the level of the corresponding miR gene product in the control sample, as being indicative of the subject having an adverse prognosis.

4. The method according to claim 3, wherein the measuring the level of the at least miR-221 gene product in the test sample is carried out by analyzing the test sample with a microarray and/or a Northern blot electrophoretic device.

5. A method of determining whether a subject has, or is at risk for developing, acute lymphomic leukemia (ALL), wherein the method comprises:
   isolating RNA from a test sample extracted from the subject, wherein the test sample comprises blood, tissue and/or bone marrow having, or suspected of having, leukemic cells and/or leukemic lymphoblasts;
   reverse transcribing the RNA isolated from the test sample to provide at least one target oligodeoxynucleotide;
   hybridizing the at least one target oligodeoxynucleotide to a microarray comprising at least one miR-221 miRNA-specific probe oligonucleotide to provide a hybridization profile for the test sample;
   determining whether the subject has, or is at risk for developing, ALL by comparing the signal of the at least one miR-221 miRNA in the hybridization profile for the test sample to the signal of a corresponding miRNA in the hybridization profile for a control sample,
   correlating an upregulated signal of the at least one miR-221 miRNA in the test sample, relative to the signal of the corresponding miRNA in the control sample, as being indicative of a diagnosis of the subject either having, or being at risk for developing, ALL.

6. A method of determining the prognosis of a subject having acute lymphomic leukemia (ALL) cancer, wherein the method comprises:
   isolating RNA from a test sample extracted from the subject;
   reverse transcribing the RNA isolated from the test sample to provide at least one target oligodeoxynucleotide;
   hybridizing the at least one target oligodeoxynucleotide to a microarray comprising at least one miR-221 miRNA-specific probe oligonucleotide to provide a hybridization profile for the test sample;
   determining the prognosis of the subject by comparing the signal of the at least one miR-221 miRNA in the hybridization profile for the test sample to the signal of a corresponding miRNA in the hybridization profile for a control sample,
   correlating an upregulated signal of the at least one miR-221 miRNA in the test sample, relative to the signal of the corresponding miRNA in the control sample, as being indicative of the subject having an adverse prognosis.

* * * * *